US009044157B2

(12) United States Patent
Adachi et al.

(10) Patent No.: US 9,044,157 B2
(45) Date of Patent: Jun. 2, 2015

(54) ASSESSMENT SYSTEM OF SPEECH SOUND LISTENING, AND METHOD AND PROGRAM THEREOF

(75) Inventors: Shinobu Adachi, Nara (JP); Koji Morikawa, Kyoto (JP); Yumiko Kato, Osaka (JP); Kazuki Kozuka, Osaka (JP)

(73) Assignee: Panasonic Intellectual Property Management Co., Ltd, Osaka (JP)

( * ) Notice: Subject to any disclaimer, the term of this patent is extended or adjusted under 35 U.S.C. 154(b) by 314 days.

(21) Appl. No.: 13/561,336

(22) Filed: Jul. 30, 2012

(65) Prior Publication Data

US 2012/0288108 A1 Nov. 15, 2012

Related U.S. Application Data

(63) Continuation of application No. PCT/JP2011/003236, filed on Jun. 8, 2011.

(30) Foreign Application Priority Data

Jun. 11, 2010 (JP) .................................. 2010-134239

(51) Int. Cl.
*H04R 29/00* (2006.01)
*A61B 5/0484* (2006.01)

(52) U.S. Cl.
CPC .................................. *A61B 5/04845* (2013.01)

(58) Field of Classification Search
CPC .. A61B 5/0476; A61B 5/04012; H04R 25/70; H04R 2225/43
USPC ............................................ 600/544; 381/60
See application file for complete search history.

(56) References Cited

U.S. PATENT DOCUMENTS

| | | | |
|---|---|---|---|
| 5,755,230 | A | 5/1998 | Schmidt |
| 6,602,202 | B2 | 8/2003 | John et al. |

(Continued)

FOREIGN PATENT DOCUMENTS

| | | |
|---|---|---|
| CN | 101365384 A | 2/2009 |
| CN | 101557753 A | 10/2009 |

(Continued)

OTHER PUBLICATIONS

S. Kuriki, Measurements of Auditory Evoked Neuromagnetic Field Using a Multichannel SQUID Magnetometer Journal of Acoustical Society of Japan, May 1992, vol. 48, No. 5, pp. 320-327 and concise explanation.

(Continued)

*Primary Examiner* — Alexander Jamal
(74) *Attorney, Agent, or Firm* — Renner, Otto, Boisselle & Sklar, LLP

(57) ABSTRACT

In an exemplary assessment system of speech sound listening, an output section presents a speech sound to a user as an auditory stimulation; a positive component determination section determines whether a positive component appears in an event-related potential of an electroencephalogram signal of the user in a range from 600-900 ms from a starting point, the starting point being a point in time at which the speech sound is presented, and outputs an assessment result as to whether the user is listening to the speech sound with strife or not; and a negative component determination section determines whether a negative component appears in the event-related potential in a range from 100-300 ms from a starting point, the starting point being the point in time at which the speech sound is presented, and outputs an assessment result as to whether the user is annoyed by the speech sound or not.

16 Claims, 22 Drawing Sheets

(56) References Cited

U.S. PATENT DOCUMENTS

| | | | |
|---|---|---|---|
| 8,805,489 B1* | 8/2014 | Ofek | 600/544 |
| 2006/0101079 A1 | 5/2006 | Morikawa | |
| 2007/0191727 A1 | 8/2007 | Fadem | |
| 2008/0033317 A1 | 2/2008 | Elberling | |
| 2009/0147148 A1 | 6/2009 | Morikawa | |
| 2010/0094162 A1 | 4/2010 | Benasich et al. | |
| 2011/0313309 A1* | 12/2011 | Nicol et al. | 600/544 |
| 2012/0072213 A1 | 3/2012 | Adachi | |

FOREIGN PATENT DOCUMENTS

| | | |
|---|---|---|
| JP | 06-114038 A | 4/1994 |
| JP | 09-038069 A | 2/1997 |
| JP | 11-511367 T | 10/1999 |
| JP | 2004-275619 A | 10/2004 |
| JP | 2008-503261 T | 2/2008 |
| WO | 2005/001677 A1 | 1/2005 |
| WO | 2007/066440 A1 | 6/2007 |
| WO | WO 2010/056947 A1 | 5/2010 |
| WO | 2011/093005 A1 | 8/2011 |

OTHER PUBLICATIONS

Hosoi et al., "Hochouki Tekigokensa No Shishin 2008", or "2008 Guidelines for Hearing Aid Suitability Test", 2008 and concise explanation.

Kazuoki Kodera, "Hochoki Fittingu No Kangaekata" (or "Concept of Hearing Aid Fitting"), Shindan to Chiroysha, 1999, p. 166 and concise explanation.

Näätänen et al., "The N1 Wave of the Human Electric and Magnetic Response to Sound: A Review and an Analysis of the Component Structure", Psychophysiology, 24, 375-425 (1987).

"Jishoukanrendeni (ERP) Manyuaru-P300 Wo Chushinni" (or "Event-Related Potential (ERP) Manual-mainly concerning P300"), edited by Kimitaka Kaga et al., Shinohara Shuppan Shinsha, 1995, p. 30. and concise explanation.

Kazuoki Kodera, "Hochoki Fittingu No Kangaekata" (or "Concept of Hearing Aid Fitting"), Shindan to Chiryosha, 1999, p. 172 and concise explanation.

Chinese search report for corresponding Chinese Application No. 201180011703.9, dated Jul. 2, 2014.

English translation of Search report for corresponding Chinese Application No. 201180011703.9, dated Jul. 2, 2014.

Co-pending U.S. Appl. No. 13/564,390, filed Aug. 1, 2012.

Hisanaga et al., Shichokakuonseis Horino Nichi•Ei Bogokan ERP Hikaku (or "ERP Comparison Between Mother Tongues of Japanese/English in Visual and Auditory Speech Processing"), the Acoustical Society of Japan, a CD-ROM of autumn research meeting preprints, Sep. 2009, pp. 567-570 and concise explanation.

Office Action for co-pending U.S. Appl. No. 12/959,513 dated Aug. 16, 2013.

Current claims for co-pending U.S. Appl. No. 12/959,513 submitted in response to Aug. 16, 2013 Office Action on Oct. 17, 2013.

International Search Report for International Application No. PCT/JP2011/003236 mailed Sep. 20, 2011.

Form PCT/ISA/237 for International Application No. PCT/JP2011/003236 dated Sep. 20, 2012 and partial English translation.

Tamesue et al., "Kiokuseishinsagyojino Souonnitaisuru Shinri-Seiritekiteiryohyokanikansuru Kisotekikousatsu (or "A Basic Discussion of Pyschological/Physiological Quantitative Evaluations with respect to Noises at Memorization Mental Tasks")", The Acoustical Society of Japan, a CD-ROM of spring research meeting preprints, Mar. 2009, pp. 1031-1032 and concise explanation.

* cited by examiner

|  |  | FLAT/DISTORTED ||
|  |  | FLAT | DISTORTED |
| --- | --- | --- | --- |
| SOUND PRES-SURE | LARGE | LF CONDITION 75−85dB | LD CONDITION 75−85dB |
| | MIDDLE | MF CONDITION 60−65dB | MD CONDITION 60−65dB |
| | SMALL | SF CONDITION 40−45dB | SD CONDITION 40−45dB |

*FIG.4A*
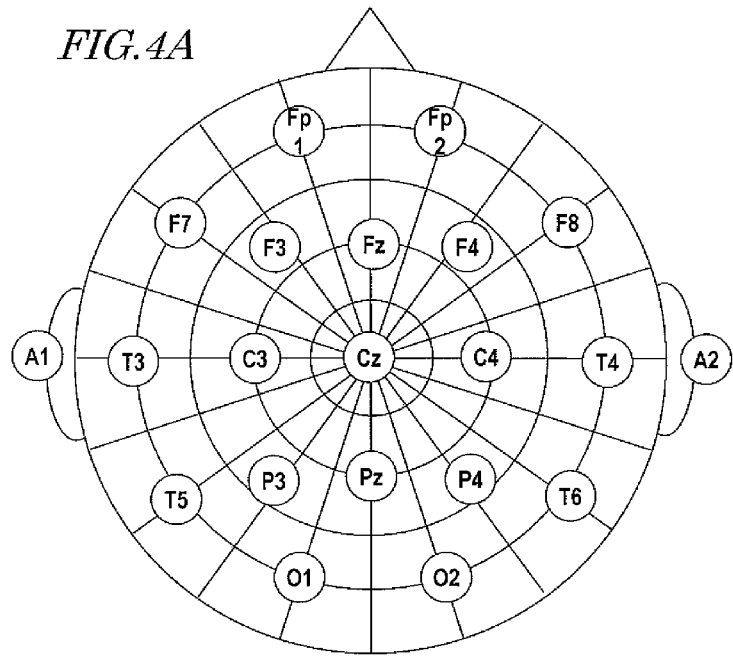
*FIG.4B*
FRONT ↑
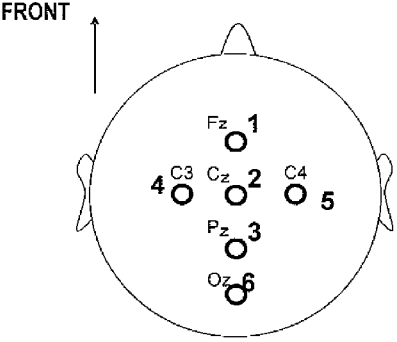
<UPPER VIEW>
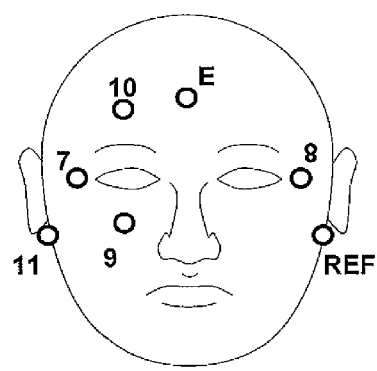
<FRONT VIEW>

*FIG.9A*

|  | PRESENT | ABSENT |
|---|---|---|
| POSITIVE COMPONENT @Pz | STRIVING | NOT STRIVING |
| NEGATIVE COMPONENT @Pz | ANNOYED | NOT ANNOYED |

*FIG.9B*

| | | NEGATIVE COMPONENT @Pz | |
|---|---|---|---|
| | | PRESENT | ABSENT |
| POSITIVE COMPONENT @Pz | PRESENT | (A) GAIN ADJUSTMENT HAS NOT BEEN MADE FOR OPTIMUM FREQUENCY | (B) AURALLY DISTINGUISHABLE WITH STRIFE |
| | ABSENT | (C) OVERALL AMPLIFICATION IS EXESSIVE | (D) AURALLY DISTINGUISHABLE IN COMFORT |

| SPEECH SOUND | AUDIO FILE | CONSONANT LABEL | GROUP |||
|---|---|---|---|---|---|
| | | | ROUGH CATEGORY | MEDIUM CATEGORY | FINE CATEGORY |
| a | a.wav | — | 0 | — | — |
| u | u.wav | — | 0 | — | — |
| o | o.wav | — | 0 | — | — |
| si | shi.wav | s | 1 | 1 | — |
| su | su.wav | s | 1 | 1 | — |
| ki | ki.wav | k | 1 | 2 | — |
| ku | ku.wav | k | 1 | 2 | — |
| ta | ta.wav | t | 1 | 2 | — |
| te | te.wav | t | 1 | 2 | — |
| to | to.wav | t | 1 | 2 | — |
| ha | ha.wav | h | 1 | 2 | — |
| yo | yo.wav | y | 2 | 1 | — |
| ri | ri.wav | r | 2 | 1 | — |
| wa | wa.wav | w | 2 | 1 | — |
| ni | ni.wav | n | 2 | 2 | 1 |
| ne | ne.wav | n | 2 | 2 | 1 |
| mo | mo.wav | m | 2 | 2 | 1 |
| ga | ga.wav | g | 2 | 2 | 2 |
| ji | ji.wav | j | 2 | 2 | 2 |
| ba | ba.wav | b | 2 | 2 | 2 |

| WORD | STRIFE | ANNOYANCE |
|---|---|---|
| sit | 1 | 0 |
| meet | 1 | 0 |
| get | 0 | 1 |
| cat | 0 | 1 |
| come | 1 | 0 |
| hot | 0 | 0 |
| law | 0 | 0 |
| book | 1 | 1 |
| blue | 1 | 1 |
| urge | 0 | 0 |
| star | 0 | 0 |
| page | 0 | 1 |
| sky | 1 | 1 |
| join | 0 | 0 |
| now | 0 | 1 |
| home | 1 | 1 |
| here | 1 | 1 |
| care | 0 | 0 |
| ... | ... | ... |

FIG.19A

STRIFE

| SPEECH SOUND | 55dB | 65dB | 75dB | 85dB |
|---|---|---|---|---|
| a | 0 | 0 | 0 | 0 |
| u | 0 | 0 | 0 | 0 |
| o | 0 | 0 | 0 | 1 |
| si | 1 | 0 | 0 | 1 |
| su | 1 | 1 | 0 | 0 |
| ki | 0 | 0 | 0 | 0 |
| ku | 0 | 0 | 0 | 0 |
| ta | 1 | 1 | 0 | 0 |
| te | 1 | 1 | 0 | 0 |
| to | 1 | 1 | 1 | 1 |
| ha | 1 | 1 | 1 | 0 |
| yo | 0 | 0 | 0 | 0 |
| ri | 0 | 0 | 0 | 0 |
| wa | 0 | 0 | 0 | 0 |
| ni | 0 | 0 | 0 | 0 |
| ne | 1 | 1 | 1 | 0 |
| mo | 1 | 1 | 1 | 1 |
| ga | 0 | 0 | 0 | 0 |
| ji | 0 | 0 | 0 | 0 |
| ba | 0 | 0 | 0 | 0 |

ANNOYANCE

| SPEECH SOUND | 55dB | 65dB | 75dB | 85dB |
|---|---|---|---|---|
| a | | | 1 | 1 |
| u | | | 0 | 1 |
| o | | | 0 | 1 |
| si | | | 1 | 1 |
| su | | | 1 | 1 |
| ki | | | 0 | 0 |
| ku | | | 0 | 0 |
| ta | | | 1 | 1 |
| te | | | 1 | 1 |
| to | | | 1 | 1 |
| ha | | | 1 | 1 |
| yo | | | 0 | 0 |
| ri | | | 0 | 0 |
| wa | | | 1 | 1 |
| ni | | | 0 | 1 |
| ne | | | 1 | 1 |
| mo | | | 1 | 1 |
| ga | | | 0 | 0 |
| ji | | | 0 | 1 |
| ba | | | 0 | 0 |

FIG.19B

ANNOYANCE

| SPEECH SOUND | 55dB | 65dB | 75dB | 85dB |
|---|---|---|---|---|
| | | | 1 | 1 |
| | | | 0 | 1 |
| | | | 0 | 1 |
| | | | 1 | 1 |
| | | | 1 | 1 |
| | | | 0 | 0 |
| | | | 0 | 0 |
| | | | 1 | 0 |
| | | | 1 | 0 |
| | | | 1 | 1 |
| | | | 1 | 1 |
| | | | 0 | 0 |
| | | | 0 | 0 |
| | | | 1 | 1 |
| | | | 0 | 1 |
| | | | 1 | 0 |
| | | | 1 | 0 |
| | | | 0 | 0 |
| | | | 0 | 1 |
| | | | 0 | 0 |

STRIFE

| SPEECH SOUND | 55dB | 65dB | 75dB | 85dB |
|---|---|---|---|---|
| a | 0 | 0 | 0 | 0 |
| u | 0 | 0 | 0 | 0 |
| o | 0 | 0 | 0 | 1 |
| si | 1 | 0 | 0 | 1 |
| su | 1 | 1 | 0 | 0 |
| ki | 0 | 0 | 0 | 0 |
| ku | 0 | 0 | 0 | 0 |
| ta | 1 | 1 | 0 | 0 |
| te | 1 | 1 | 0 | 0 |
| to | 1 | 1 | 1 | 1 |
| ha | 1 | 1 | 1 | 0 |
| yo | 0 | 0 | 0 | 0 |
| ri | 0 | 0 | 0 | 0 |
| wa | 0 | 0 | 0 | 0 |
| ni | 0 | 0 | 0 | 0 |
| ne | 1 | 1 | 0 | 0 |
| mo | 1 | 1 | 1 | 0 |
| ga | 0 | 0 | 0 | 0 |
| ji | 0 | 0 | 0 | 0 |
| ba | 0 | 0 | 0 | 0 |

ASSESSMENT SYSTEM OF SPEECH SOUND LISTENING, AND METHOD AND PROGRAM THEREOF

This is a continuation of International Application No. PCT/JP2011/003236, with an international filing date of Jun. 8, 2011, which claims priority of Japanese Patent Application No. 2010-134239, filed on Jun. 11, 2010, the contents of which are hereby incorporated by reference.

BACKGROUND

1. Technical Field

The present application relates to a technique of assessing whether a user has been able to comfortably listen to a speech sound or not. More specifically, the present application relates to a comfortableness assessment system of speech sound listening for assessing level of comfortableness in listening to speech sounds, for the "fitting" of a hearing aid or the like to provide a sound of appropriate loudness for each individual user by adjusting the amount of amplification of sounds with respect to each frequency.

2. Description of the Related Art

In recent years, people suffering from presbycusis are increasing in number due to the aging society. Even among the young, due to increased opportunities for listening to loud music for long hours as well as other influences, there is an increasing number of people suffering from hypacusia associated with acoustic traumas. Moreover, due to the downsizing and improved performance of hearing aids, users feel less of a psychological barrier against wearing hearing aids. Against this background, there is an increasing number of users who wear hearing aids on a daily basis in order to improve their conversational aural distinction abilities.

A hearing aid is a device for compensating for the deteriorated hearing of a user by increasing the amplitude of signals of specific frequencies, among various frequencies that compose sounds that are difficult for the user to hear. The amount of sound amplification which a user desires in a hearing aid varies depending on the level of deterioration in the hearing of the user. Therefore, before beginning use of a hearing aid, "fitting" is required for adjusting the amount of sound amplification in accordance with the hearing of each user.

Fitting is performed in such a manner that the output sound pressure (i.e. fluctuations in air pressure that are perceivable as a sound) of each frequency from a hearing aid is at an MCL (most comfortable level: a sound pressure level that is felt comfortable to a user). Thus, it is considered that appropriate fitting is yet to be attained under (1) an insufficient amount of amplification, or (2) an excessive amount of amplification. For example, under an insufficient amount of amplification, aural distinction of audios is not achieved, thus falling short of the purpose of wearing a hearing aid. Under an excessive amount of amplification, although distinction of audios may be possible, there is a problem in that the user may feel annoyance, which prevents them from using the hearing aid over a long time. Therefore, a fitting needs to be done in such a manner that neither (1) nor (2) occurs.

A first step of fitting is measuring an audiogram. An "audiogram" is an evaluation of a threshold value defining a smallest sound pressure of a pure tone that allows it to be heard; for example, a diagram in which, for each of a number of sounds of different frequencies, the smallest sound pressure level (decibel value) that the user can aurally comprehend is plotted against frequency (e.g., 250 Hz, 500 Hz, 1000 Hz, 2000 Hz, 4000 Hz).

Next, based on a fitting theory, which is a mathematical function for estimating an amount of amplification for each frequency, an amount of amplification for each frequency is determined from the resultant audiogram.

However, from an audiogram/fitting theory-based adjustment alone, one cannot know whether an optimum fitting has been realized for improving the intelligibility in aural distinction of conversations. Possible reasons are, for example: an audiogram is not in one-to-one correspondence with a conversational aural distinction ability; a person suffering from hypacusia has a narrow range of sound pressure that is felt to him or her as an appropriate loudness, which makes adjustment difficult; and so on.

Therefore, upon wearing a hearing aid which has been determined and adjusted by the aforementioned method, a hearing aid suitability test is to be carried out (see, for example, Hiroshi HOSOI et al., HOCHOUKI TEKIGO-KENSA NO SHISHIN 2008, or "2008 Guidelines For Hearing Aid Suitability Test", 2008). There are two mandatory test items in a hearing aid suitability test: (1) measurement of a speech sound intelligibility curve, and (2) measurement of an ambient noise tolerance level.

In the measurement of a speech sound intelligibility curve, both when wearing a hearing aid and when not wearing a hearing aid (naked ear), monosyllabic speech sounds are presented at 55 dB SPL (Sound pressure level), 65 dB SPL, 75 dB SPL, and 85 dB SPL; and the speech sound intelligibility at each sound pressure level is plotted for comparison. Then, if the intelligibility appears improved when wearing a hearing aid relative to when not wearing a hearing aid, it is determined as suitable.

As used herein, "speech sound intelligibility" refers to a level as to how well a monosyllabic speech sound has been aurally comprehended. A speech sound intelligibility reflects a level of aural distinction during conversations. A "monosyllabic speech sound" means either a single vowel or a combination of a consonant and a vowel (e.g., "あ (a)"/"だ (da)"/"し (shi)").

Speech sound intelligibility is assessed through the following procedure (see, for example, Kazuoki KODERA, "HOCHOKI FITTINGU NO KANGAEKATA (or "Concept of Hearing Aid Fitting"), Shindan To Chiryosha, 1999, p. 166). First, audios in the 67S list (20 speech sounds) proposed by the Japan Audiological Society are reproduced one by one, which a user is allowed to hear. Next, through oral explanation, writing, or other methods, the user is asked to answer which speech sound he or she has aurally comprehended the presented speech sound to be. Then, an evaluator matches the answers against the speech sounds which have been presented, and calculates a correctness rate, which is a rate of speech sounds that have been correctly aurally comprehended among the total of 20 speech sounds. This correctness rate is the speech sound intelligibility.

Various techniques have been disclosed in the past concerning methods of speech sound intelligibility assessment. For example, Japanese Laid-Open Patent Publication No. 9-038069 discloses a speech sound intelligibility assessment method which employs a personal computer (PC) to automatically perform correctness determination. This publication proposes a method in which monosyllabic audios are presented to a user by using a PC; the user is asked to answer with a mouse or by touching a pen to the display; the answers are received as inputs to the PC; and correctness determinations as to the presented audios and answer inputs are automatically made. Since answer inputs are received with a mouse or a pen touch, there is no need for the evaluator to distinguish and analyze the user's answers (which are given by oral explanation or writing), whereby the trouble of the evaluator is reduced.

Moreover, for example, Japanese Laid-Open Patent Publication. No. 6-114038 discloses a speech sound intelligibility assessment method in which, after audio presentation, possible choices of speech sounds are presented in the form of text characters. In this publication, choices are limited to only a small number so that the relevant speech sound can be found among the small number of characters, whereby the user's trouble of finding the character is reduced.

On the other hand, in the measurement of an ambient noise tolerance level, sounds which are read aloud are simultaneously presented with ambient noise, and after the sounds which are read aloud are heard, an assessment is made as to whether the ambient noise is tolerable or not (KODERA, et al., supra). Specifically, sounds which are read aloud are presented at 65 dB SPL, and ambient noise is presented at 55 dB SPL, and a subjective impression as to whether the ambient noise is tolerable or not is to be reported. As the subjective impression, it is to be reported whether one can endure using a hearing aid when listening to sounds which are read aloud in the presence of noise, or it is difficult to wear a hearing aid in the presence of noise. The former case is determined as suitable, whereas the latter case is determined as unsuitable.

SUMMARY

The prior art technique needs further improvement in view of comfortableness in assessing a user state concerning comfortableness of speech sound listening.

One non-limiting, and exemplary embodiment provides a technique to realize a comfortableness assessment system of speech sound listening for assessing a user state concerning comfortableness of speech sound listening.

In one general aspect, an assessment system of speech sound listening according to the present disclosure comprises: a biological signal measurement section configured to measure an electroencephalogram signal of a user; a presented-speech sound determination section configured to determine a monosyllabic speech sound to be presented, by referring to a speech sound database retaining a plurality of monosyllabic speech sounds; an output section configured to present a speech sound determined by the presented-speech sound determination section to the user as an auditory stimulation; a positive component determination section configured to determine whether a positive component appears in an event-related potential of the electroencephalogram signal in a range from 600 ms to 900 ms from a starting point, the starting point being a point in time at which the speech sound is presented, and configured to output an assessment result as to whether the user is listening to the speech sound with strife or not in accordance with a result of determination; and a negative component determination section configured to determine whether a negative component appears in an event-related potential of the electroencephalogram signal in a range from 100 ms to 300 ms from a starting point, the starting point being the point in time at which the speech sound is presented, and configured to output an assessment result as to whether the user is annoyed by the speech sound or not in accordance with a result of determination.

According to the above aspect, it is possible to improve comfortableness in assessing a user state concerning comfortableness of speech sound listening.

These general and specific aspects may be imple-mented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIG. 4A is a diagram showing electrode positions according to the International 10-20 system, and FIG. 4B is a diagram showing electrode positioning as to how electrodes are worn in the present experiment.

FIG. 9A is a diagram showing correspondence between the presence or absence of a positive component/negative component and strife/annoyance determinations, and FIG. 9B is a diagram showing correspondence between the presence or absence of a positive component and a negative component and acoustic aiding process assessments, as compiled by the inventors.

FIG. 17 is a diagram showing an exemplary result of assessing strife and annoyance for different monosyllabic words.

FIGS. 19A and 19B are diagrams showing examples of data accumulation in a result accumulating DB 85.

DETAILED DESCRIPTION

Figure 1:
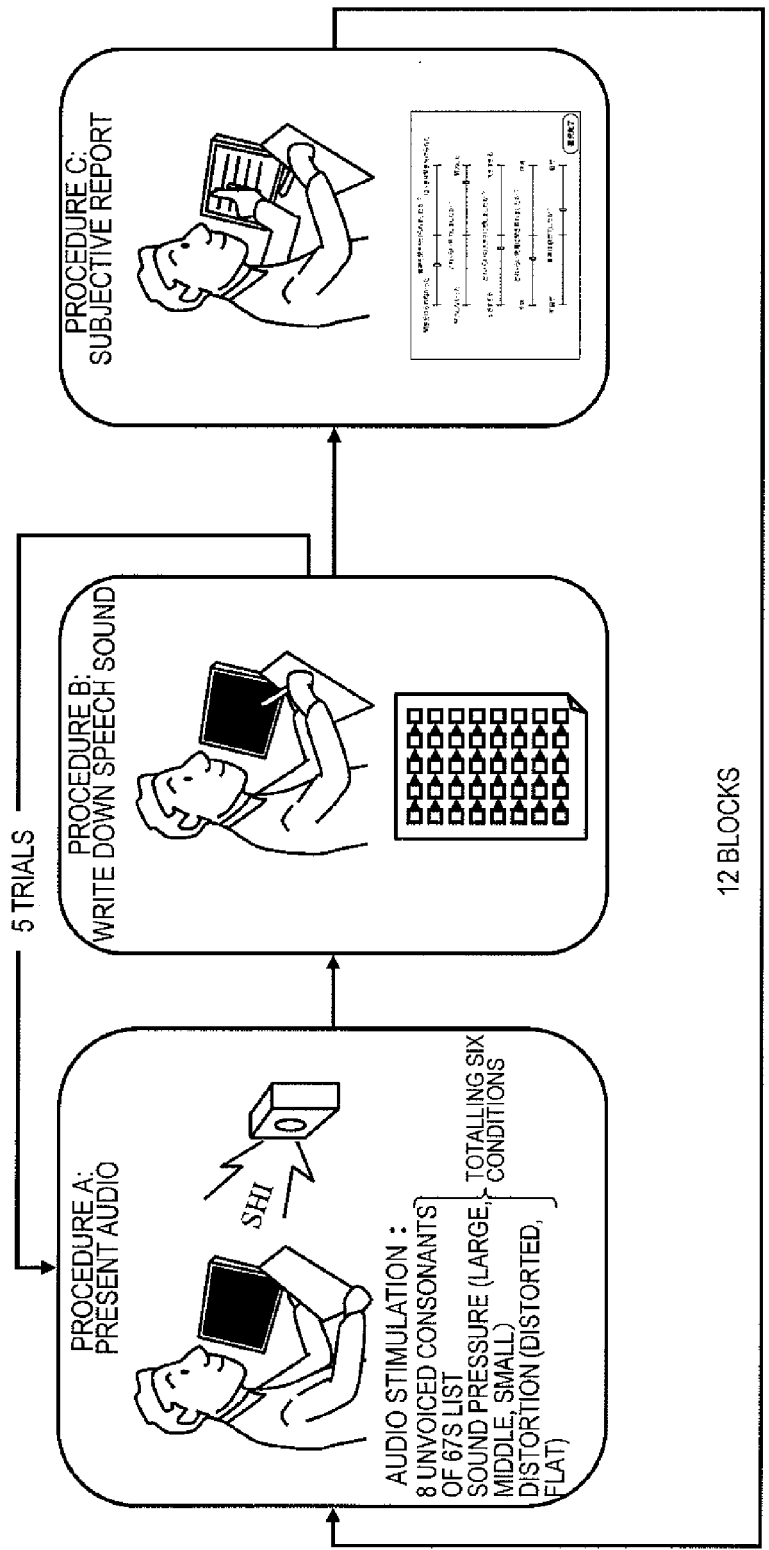
FIG. 1 is a diagram showing the experimental procedure of an electroencephalogram measurement experiment in outline.

In the speech sound intelligibility curve measurement of the aforementioned hearing aid suitability test of the related art, a suitable state is determined based only on speech sound intelligibility, while giving no consideration as to whether the speech sound listening is comfortable or not. Therefore, even though the comfortableness at speech sound listening may be low, if the intelligibility which is obtained when wearing a hearing aid is higher than that obtained when not wearing a hearing aid, the acoustic aiding process is assessed as suitable. On the other hand, in the measurement of an ambient noise tolerance level, an assessment is made as to whether the ambient noise is tolerable, while making no assessment as to the comfortableness of the speech sound listening itself. In these assessments, even an acoustic aiding process which provides a low comfortableness of speech sound listening, such that hearing fatigue is likely to occur, may have been determined as suitable. Low comfortableness is a burden on a user who wears a hearing aid on a daily basis.

An assessment system of speech sound listening according to the present disclosure comprises: a biological signal measurement section configured to measure an electroencephalogram signal of a user; a presented-speech sound determination section configured to determine a monosyllabic speech sound to be presented, by referring to a speech sound database retaining a plurality of monosyllabic speech sounds; an output section configured to present a speech sound determined by the presented-speech sound determination section to the user as an auditory stimulation; a positive component determination section configured to determine whether a positive component appears in an event-related potential of the electroencephalogram signal in a range from 600 ms to 900 ms from a starting point, the starting point being a point in time at which the speech sound is presented, and configured to output an assessment result as to whether the user is listening to the speech sound with strife or not in accordance with a result of determination; and a negative component determination section configured to determine whether a negative component appears in an event-related potential of the electroencephalogram signal in a range from 100 ms to 300 ms from a starting point, the starting point being the point in time at which the speech sound is presented, and configured to output an assessment result as to whether the user is annoyed by the speech sound or not in accordance with a result of determination.

The assessment system may further comprise an event-related potential processing section configured to take an arithmetic mean of event-related potentials of the electroencephalogram signal, wherein the speech sound is classified based on at least one of a speech sound type and a sound pressure level of presentation, and the event-related potential processing section takes an arithmetic mean of event-related potentials of the electroencephalogram signal obtained when speech sounds belonging to a same classification are presented.

The positive component determination section may determine that the positive component is present when a zone average potential of an event-related potential of the electroencephalogram signal in a range from 600 ms to 900 ms from a starting point, the starting point being a point in time at which the speech sound is presented, is equal to or greater than a predetermined first threshold value, and determine that the positive component is absent when the zone average potential is smaller than the first threshold value.

The positive component determination section may output an assessment result that the user is listening to the speech sound with strife when determining that the positive component is present, and output an assessment result that the user is hearing the speech sound without strife when determining that the positive component is absent.

The negative component determination section may determine that the negative component is present when a peak latency of a negative component in a range from 100 ms to 300 ms from a starting point, the starting point being a point in time at which the speech sound is presented, is shorter than a predetermined second threshold value, and determine that the negative component is absent when the peak latency of the negative component is equal to or greater than the second threshold value.

The negative component determination section may output an assessment result that the user is annoyed by the speech sound when determining that the negative component is present, and output an assessment result that the user is not annoyed by the speech sound when determining that the negative component is absent.

In the speech sound database, an audio, consonant information, and a group concerning probability of confusion may be associated with each of the plurality of speech sounds.

The assessment system may further comprise a result accumulating database configured to accumulate results of determination by the positive component determination section and the negative component determination section, wherein with respect to at least one sound pressure level, the result accumulating database calculates a proportion of speech sounds, consonants, or groups concerning probability of confusion for which the positive component determination section has determined that the positive component is absent, and a proportion of speech sounds, consonants, or groups concerning probability of confusion for which the negative component determination section has determined that the negative component is absent, and generates assessment results by using results of the calculation.

In the result accumulating database, information for assessing whether the user is listening to the speech sound with strife and whether the user is annoyed by the speech sound may be accumulated with respect to each speech sound, each consonant, or each group concerning probability of confusion.

In the result accumulating database, information for assessing whether the user is listening to the speech sound with strife and whether the user is annoyed by the speech sound may be accumulated with respect to each speech sound and each sound pressure level.

The presented-speech sound determination section may determine a sound pressure level of the presented audio.

The assessment system may further comprise an acoustic aiding processing section configured to select an acoustic aiding process type for the speech sound determined by the presented-speech sound determination section for presentation, and configured to modify speech sound data retained in the speech sound database based on the selected acoustic aiding process.

The assessment system may further comprise a result accumulating database configured to accumulate results of determination by the positive component determination section and the negative component determination section, wherein in the result accumulating database, information for assessing whether the user is listening to the speech sound with strife and whether the user is annoyed by the speech sound is accumulated with respect to each speech sound and each acoustic aiding process.

An assessment apparatus of speech sound listening according to the present disclosure comprises: a presented-speech sound determination section configured to, by referring to a speech sound database retaining a plurality of monosyllabic speech sounds, determine one of the monosyllabic speech sounds to be presented via an output section to a user as an auditory stimulation; a positive component determination section configured to, with respect to an electroencephalogram signal measured by a biological signal measurement section for measuring an electroencephalogram signal of the user, determine whether a positive component appears in an event-related potential of the electroencephalogram signal in a range from 600 ms to 900 ms from a starting point, the starting point being a point in time at which the speech sound is presented; and a negative component determination section configured to determine whether a negative component appears in an event-related potential of the electroencephalogram signal in a range from 100 ms to 300 ms from a starting point, the starting point being the point in time at which the speech sound is presented.

A assessment method of speech sound listening according to the present disclosure comprises the steps of: measuring an electroencephalogram signal of a user; determining a monosyllabic speech sound to be presented, by referring to a speech sound database retaining a plurality of monosyllabic speech sounds; presenting a speech sound determined by the step of determining to the user as an auditory stimulation; determining whether a positive component appears in an event-related potential of the electroencephalogram signal in a range from 600 ms to 900 ms from a starting point, the starting point being a point in time at which the speech sound is presented; outputting an assessment result as to whether the user is listening to the speech sound with strife or not in accordance with a result of determination; determining whether a negative component appears in an event-related potential of the electroencephalogram signal in a range from 100 ms to 300 ms from a starting point, the starting point being the point in time at which the speech sound is presented; and outputting an assessment result as to whether the user is annoyed by the speech sound or not in accordance with a result of determination.

A computer program according to the present disclosure is a computer program stored on a non-transitory computer-readable medium, and to be executed by a computer mounted in a speech sound intelligibility assessment system, wherein the computer program causes the computer in the speech sound intelligibility assessment system to execute the steps of: receiving a measured electroencephalogram signal of a user; determining a monosyllabic speech sound to be presented, by referring to a speech sound database retaining a plurality of monosyllabic speech sounds; presenting a speech sound determined by the step of determining to the user as an auditory stimulation; determining whether a positive component appears in an event-related potential of the electroencephalogram signal in a range from 600 ms to 900 ms from a starting point, the starting point being a point in time at which the speech sound is presented; outputting an assessment result as to whether the user is listening to the speech sound with strife or not in accordance with a result of determination; determining whether a negative component appears in an event-related potential of the electroencephalogram signal in a range from 100 ms to 300 ms from a starting point, the starting point being the point in time at which the speech sound is presented, and outputting an assessment result as to whether the user is annoyed by the speech sound or not in accordance with a result of determination.

According to the present disclosure, based on the presence or absence of a positive component at a latency of about 750 ms and a negative component at a latency of about 200 ms in an electroencephalogram of a user after an audio is presented, determinations are made as to how much strife was made in listening to the speech sound (strife) and how annoying the speech sound was felt to be (annoyance), thus defining comfortableness of speech sound listening. Then, an acoustic aiding process assessment is realized, not only from the perspective of intelligibility (which indicates how well the speech sound has been aurally distinguished) but also from the perspective of comfortableness of speech sound listening. Through comfortableness assessment based on the factors of strife and annoyance, the user is enabled to select an acoustic aiding process which is highly comfortable (i.e., not requiring strife and not felt as annoying), and not inducing fatigue even when a hearing aid is worn for a long time.

Hereinafter, with reference to the attached drawings, embodiments of a comfortableness assessment system of speech sound listening according to the present disclosure (hereinafter referred to as a "comfortableness assessment system") will be described.

A comfortableness assessment system according to the present disclosure is used for making an assessment concerning, as a user state when listening to speech sounds, how comfortably a user has listened to speech sounds, by utilizing his or her electroencephalogram. More specifically, on the premise of presenting a monosyllabic speech sound in the form of an audio and asking the user to aurally distinguish the audio, the present system assesses a comfortableness of speech sound listening, where an event-related potential of the user electroencephalogram which is measured based on audio presentation as a starting point is utilized as an index. In the present specification, an "event-related potential" means a portion of an electroencephalogram, referring to a transient potential fluctuation in the brain which occurs in temporal relationship with an external or internal event. To "present an audio" means to output an auditory stimulation (also referred to as an "audio stimulation"), e.g., outputting an audio through a loudspeaker. Note that the type of loudspeaker may be arbitrary. It may be a loudspeaker which is placed on the floor or on a stand, or may be loudspeakers in the form of headphones. However, in order to correctly perform an assessment, any loudspeaker needs to be able to accurately make an output at a designated sound pressure.

The inventors have arrived at the concept that a comfortableness of speech sound listening is definable in terms of two elements: (1) "strife" concerning how much effort has been made to aurally distinguish a speech sound; and (2) "annoyance" indicating how annoying (i.e., loud) a speech sound has been felt as. This concept is unprecedentedly obtained through a speech sound intelligibility assessment and through a detailed analysis of the user state at the time of assessment, as will be specifically described below.

In a speech sound intelligibility assessment, a ◯/X assessment is made as to whether each speech sound was aurally distinguished, and the number of speech sounds that have been successfully aurally distinguished is divided by the number of speech sounds subjected to assessment (i.e., 20 in the case of the 67S list). Therefore, the result does not reflect any user state when listening to speech sounds.

However, in actuality, there may be cases where an aural distinction is made in comfort as well as cases where an aural distinction is made in discomfort. A speech sound intelligibility assessment is a short-time assessment which takes place at a hearing aid shop, and therefore a user under assessment will try to aurally distinguish speech sounds with maximum strife. The fact as to whether the user feels annoyed or not is irrelevant to the assessment; therefore, unless it is so annoying that it is intolerable, the user will be willing to carry out the assessment task even if slightly annoyed.

However, in the case where a hearing aid is worn for long hours on a daily basis, it would be difficult to always maintain maximum strife to try to aurally comprehend conversations, and it would be a burden to the user if he or she had to tolerate acoustic annoyance for a long time.

In view of these situations, the inventors have arrived at the thought that assessment needs to be made separately with respect to different user states when listening to speech sounds: when neither "strife" nor "patience for annoyance" is needed; and when some "strife" or "patience for annoyance" is needed. Thus, the inventors have identified these to be factors of comfortableness at speech sound listening. Since strife and annoyance pertain to entirely distinct processes in the brain, there is a possibility that these can be separately assessed through electroencephalogram measurement.

1. Experimental Outline

With a view to realizing comfortableness assessment of speech sound listening, the inventors have conducted the following experiment for identifying electroencephalogram characteristic components which reflect strife and annoyance.

On the premise of presenting a monosyllabic speech sound in the form of an audio and asking a user to think of a speech sound corresponding to the audio, an electroencephalogram measurement experiment was conducted where an event-related potential was measured based on audio presentation as a starting point. In the experiment, it was asked that subjective reports on strife/annoyance with respect to speech sound listening be made, thus to measure subjective perceptions concerning strife/annoyance. Then, based on the subjective reports on strife/annoyance, an arithmetic mean of event-related potentials for each element was taken.

It was thus found, in the event-related potential based on audio presentation as a starting point, that: (1) when there is high strife for aural distinction of audios, a positive component is induced at the parietal at a latency of about 750 ms, as compared to the case where there is low strife for aural distinction of audios; and (2) independently from the aforementioned positive component, a negative component (N1 component) at a latency of about 200 ms will have its latency decreased as the annoyance with respect to the audio increases. "Latency" represents, based on the point in time of presenting an audio stimulation as a starting point, an amount of time which lapses before a positive component or negative component peak appears.

From these findings, it has been found that: (1) an assessment of strife in speech sound listening can be made on the basis of the presence or absence of a positive component in an event-related potential at a latency of about 750 ms based on audio presentation as a starting point; and (2) an assessment of annoyance in speech sound listening can be made based on the presence or absence of a negative component (N1 component) at a latency of about 200 ms. With this technique, as a user state when listening to speech sounds, an assessment as to whether the user was striving and/or being annoyed can be made in an objective and quantitative manner.

These will be described in more detail below. Firstly, an electroencephalogram measurement experiment which was conducted by the inventors in order to realize comfortableness assessment of speech sound listening will be described. Thereafter, as an embodiment, an outline of a speech sound listening comfortableness assessment apparatus for assessing comfortableness of speech sound listening, as well as a construction and operation of a comfortableness assessment system which includes the speech sound listening comfortableness assessment apparatus, will be described.

2. Electroencephalogram Measurement Experiment

In the electroencephalogram measurement experiment, a relationship between the subjective reports on strife and annoyance which were acquired after audio presentation and an event-related potential based on the audio as a starting point was examined. Hereinafter, with reference to FIG. 1 to FIG. 8, the experimental setting and experimental results of the electroencephalogram measurement experiment will be described.

Thirteen undergraduate or graduate students with normal hearing participated in the experiment.

FIG. 1 shows the experimental procedure of the electroencephalogram measurement experiment in outline. First, a monosyllabic audio was presented in Procedure A. The particulars of the presented audios will be described later. Next, in Procedure B, each participant was allowed to hear an audio, and asked to write down a hiragana corresponding to the audio as he or she heard it. The conditions of the presented audios were kept unvaried, while only the speech sound type was varied. Procedures A and B were repeated five times (5 trials). Then, in Procedure C, the participant was asked to make a subjective evaluation concerning strife/annoyance and the like with respect to each audio that was presented in Procedure A. The subjective evaluation was based on a visual analog scale (100-step evaluation), and was made by using a touch panel. This was repeated 12 blocks, where 1 block consisted of Procedure A to Procedure C as above (totaling 60 trials). For each block, the sound pressure and distortion conditions of the presented audios were varied in random order.

Figure 2:
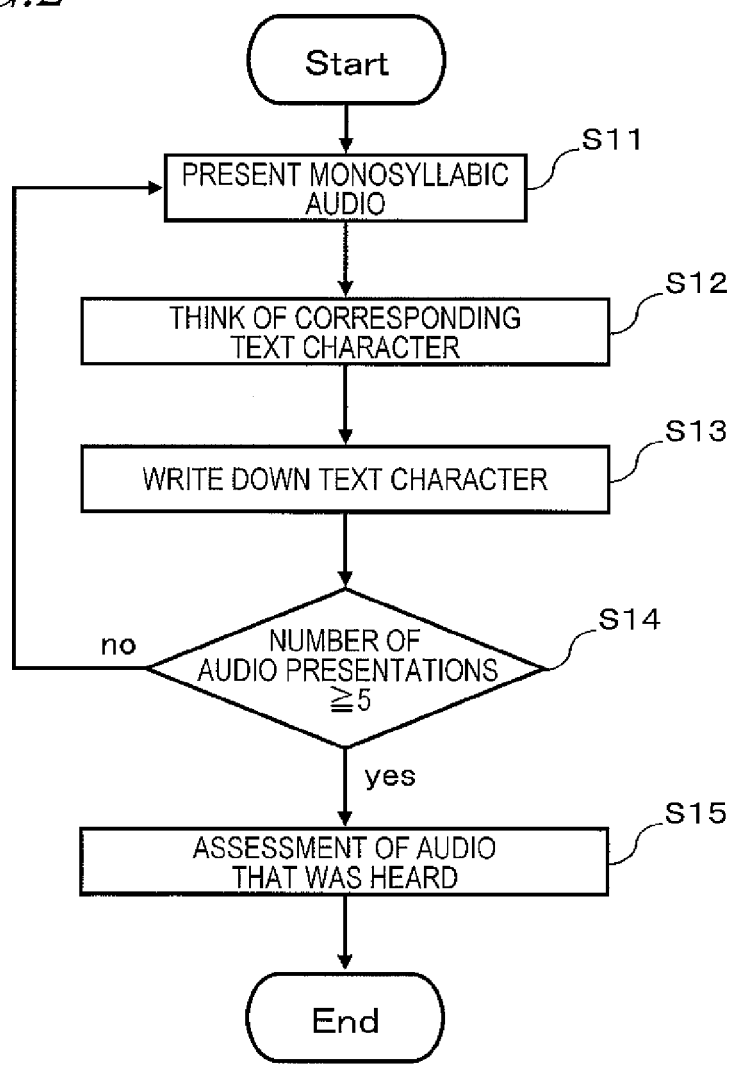
FIG. 2 is a flowchart showing a procedure corresponding to one block.

FIG. 2 is a flowchart showing a procedure corresponding to one block.

At step S11, a monosyllabic audio is presented to an experimental participant.

At step S12, the participant thinks of a corresponding text character upon hearing the monosyllabic audio.

At step S13, the participant writes down the text character corresponding to the audio as he or she heard it.

At step S14, the number of times that the audios have been presented is counted. While the number of presentations is equal to or less than 4, the process returns to S11. When the number of presentations reaches 5, the process proceeds to S15, where the number of presentations is reset.

At step S15, the participant answers with a subjective perception of the audio which was heard at step S11.

From among unvoiced consonants which are supposed to induce mistakes in aural comprehension, 8 sounds (シ (shi), ス (su), キ (ki), ク (ku), タ (ta), テ (te), ト (to), ハ (ha)) in the 67S list as proposed by the Japan Audiological Society were selected as the speech sounds to be presented as stimulations. Speech sounds with adjusted frequency gains were used, thus to control the comfortableness factors of strife and annoyance for participants with normal hearing. A "frequency gain" refers to a gain (i.e., a circuit gain or rate of amplification) for each of a number of frequency bands.

For frequency gain adjustment, three sound pressure levels (Large, Middle, Small)×two distortion levels (Flat, Distorted) were set, totaling six conditions, as are detailed in (1) to (6) below. In the present specification, large sound pressure and flat (no distortion) conditions may be referred to as LF condition (an acronym of Large and Flat), for example.

(1) LF (Large Flat) condition: the gain was increased by 20 dB across entire frequency band, meant as an audio which had a large sound pressure and was easy to aurally distinguish. (2) LD (Large Distorted) condition: the gain was universally increased by 20 dB relative to the MD condition, meant as an audio which had a large sound pressure but was difficult to aurally distinguish. (3) MF (Middle Flat) condition: the frequency gain was not modified, meant as an audio which had a large sound pressure and was easy to aurally distinguish. (4) MD (Middle Distorted) condition: from an audio of the LF condition, the gain at frequencies of 250 Hz to 16 kHz was gradually adjusted (decreased) to −30 dB, meant as an audio which was difficult to aurally distinguish. (5) SF (Small Flat) condition: the gain was decreased by 20 dB across the entire frequency band, meant as an audio which had a small sound pressure but was easy to aurally distinguish. (6) SD (Small Distorted) condition: the gain was universally decreased by 20 dB relative to the MD condition, meant as an audio which had a small sound pressure and was difficult to aurally distinguish.

Figures 3A, 3B:
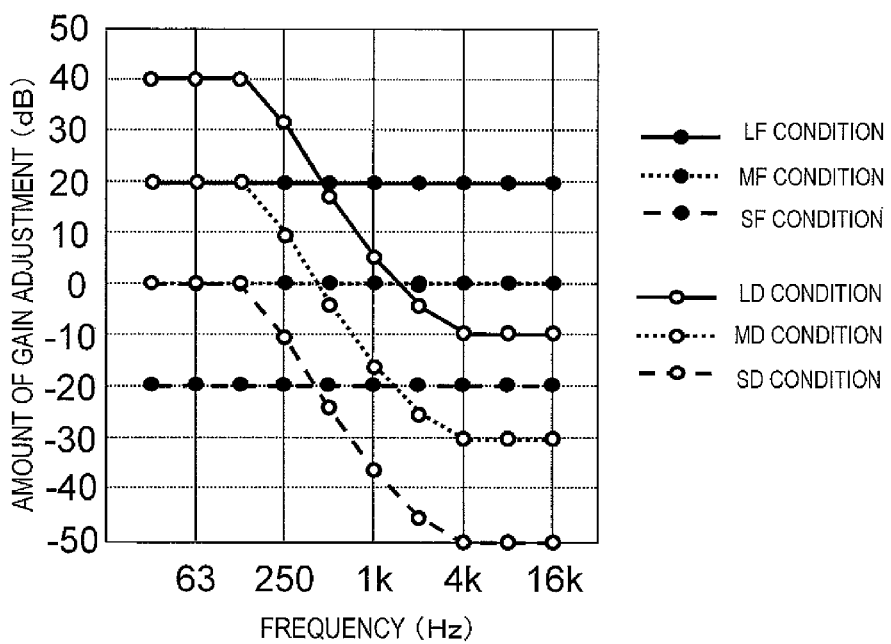
FIG. 3A is a diagram showing six conditions of audio and distortion.
FIG. 3B is a diagram showing amounts of gain adjustment for different frequencies.

FIG. 3A shows classification of six conditions concerning sound pressure level and distortion. FIG. 3B shows amounts of gain adjustment for different frequencies. The reason why the frequency gain for the high-frequency band was decreased is in order to reproduce a typical pattern of hypacusia of elderly people, i.e., gradual high tone loss. The audio stimulations were presented from a loudspeaker with flat frequency characteristics.

Each electroencephalogram was recorded from electrodes placed at the Fz, Cz, Pz, C3, and C4 (International 10-20 system) on the scalp, the right and left temples, and above and below the right eye, on the basis of the right mastoid. A "mastoid" is a protrusion of the cranium below the hind root of an ear. FIG. 4A shows electrode positions according to the International 10-20 system (10-20 System), whereas FIG. 4B shows electrode positioning as to how electrodes were worn in the present experiment. The sampling frequency was 200 Hz, and the time constant was 1 second. It was subjected to a 0.05 to 6 Hz digital band-pass filter off-line. As an event-related potential in response to an audio presentation, a waveform from −200 ms to 1000 ms was cut out based on the point of audio presentation as a starting point. Herein, "−200 milliseconds" signifies a point in time which is 200 milliseconds before the point of audio presentation.

Hereinafter, distribution of results of subjective evaluation and threshold value setting will be described.

First, results of subjective evaluation will be described. Based on the results of subjective evaluation, presence or absence of strife/annoyance was labeled relative to a threshold value which was determined for each participant based on a method describe below. Hereinafter, these subjective evaluation labels will be treated as the user states when listening to speech sounds.

Figure 5:
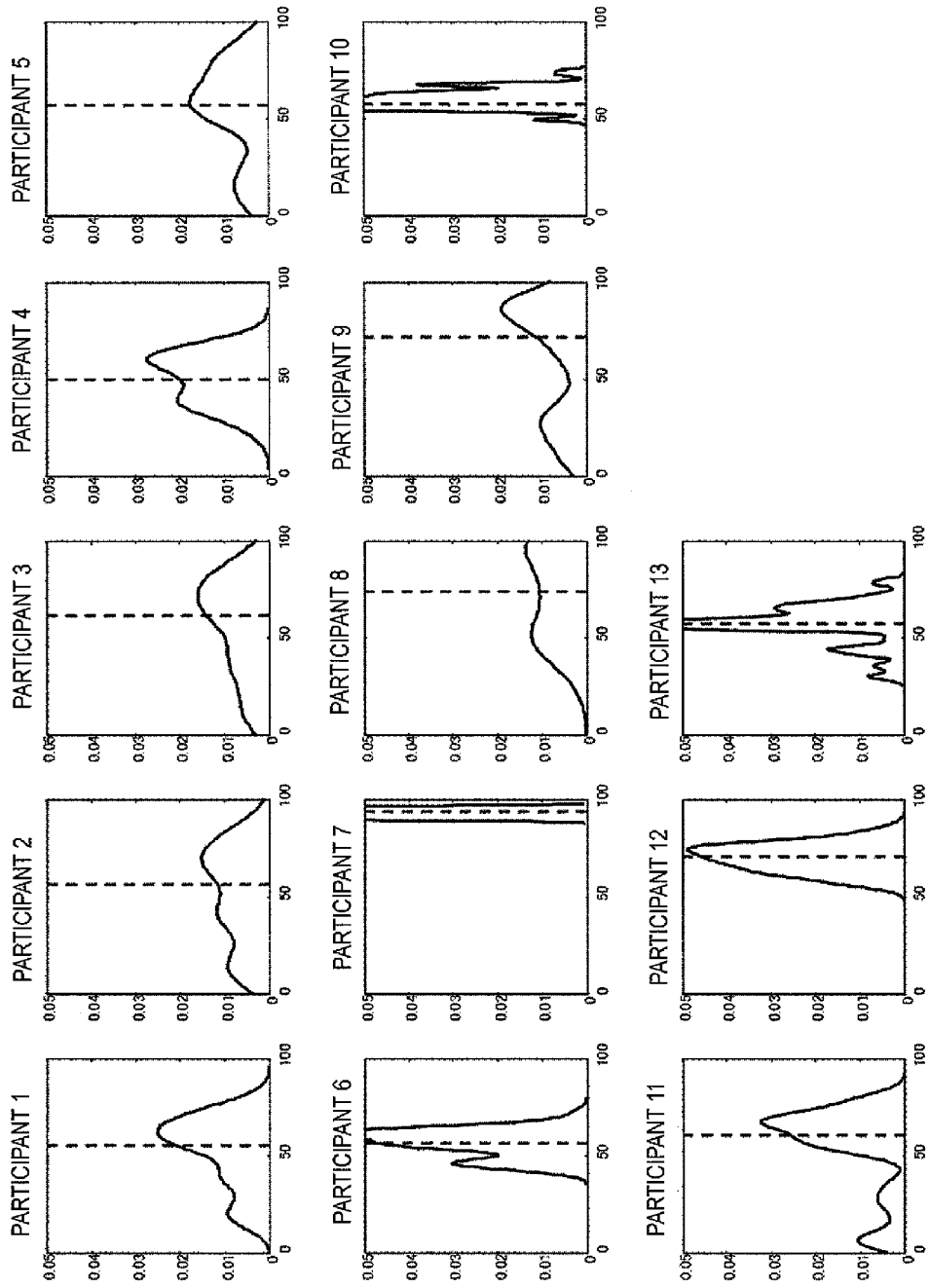
FIG. 5 is a diagram showing results of subjective evaluation of different participants concerning strife.

FIG. 5 shows subjective report regarding strife, that is, results of subjective evaluation of different participants concerning strife. Each graph of FIG. 5 shows a proportion within all trials. Each solid line in FIG. 5 shows a distribution of results of subjective evaluation, whereas each broken line shows a threshold value at which subjective evaluations (high strife/low strife) are split. Since subjective evaluation admits of large individual differences, the threshold value was determined based on the ordinal ranks of evaluation results (i.e., 1 to 100 on the visual analog scale) of each individual person. Specifically, a value which marks a median ordinal rank among the evaluation results of each individual person was defined as the threshold value. Herein, identical evaluation results were treated as pertaining to the same subjective evaluation.

Figure 6:
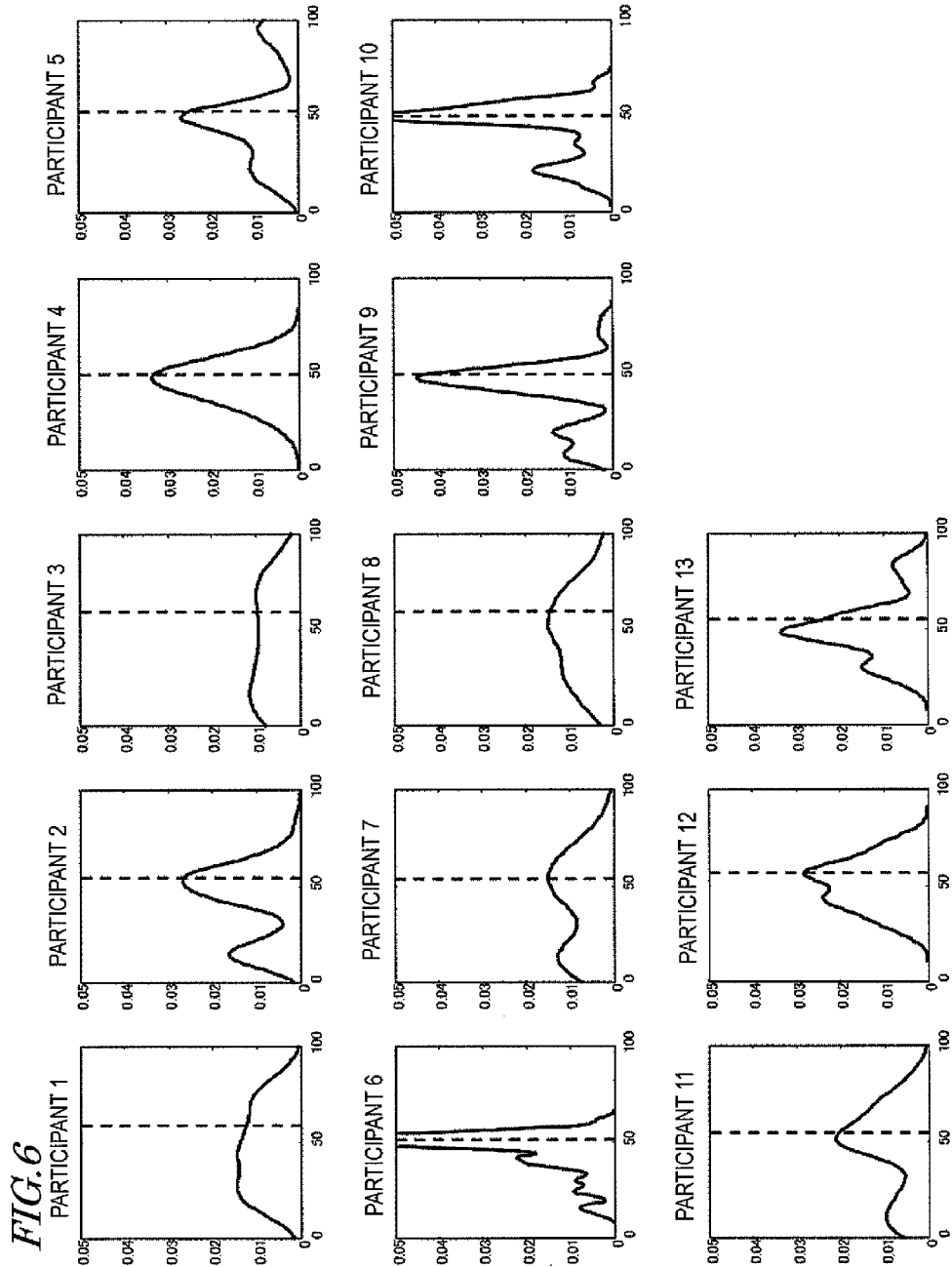
FIG. 6 is a diagram showing results of subjective evaluation of different participants concerning annoyance.

FIG. 6 shows subjective report regarding annoyance, that is, results of subjective evaluation of different participants concerning annoyance. Each graph of FIG. 6 shows a proportion within all trials. Each solid line in FIG. 6 shows a distribution of results of subjective evaluation, whereas each broken line shows a threshold value at which subjective evaluations ("annoying"/"not annoying") are split. As in the case of strife, the inventors have determined the threshold value based on the ordinal ranks of evaluation results (i.e., 1 to 100 on the visual analog scale) of each individual person. Specifically, among the ordinal ranks of evaluation values of each individual person, the inventors have defined those evaluation values which account for a greater ⅓ as "annoying", and anything else as "not annoying", thus finding a threshold value. Herein, identical evaluation results were treated as pertaining to the same subjective evaluation.

Next, experimental results concerning strife will be described.

Hereinafter, event-related potential results will be described. First, results of taking an arithmetic mean based on high strife/low strife, as labeled based on results of subjective evaluation, Next, a result of taking an arithmetic mean based on the "annoying"/"not annoying" criteria will be described.

Figure 7A:
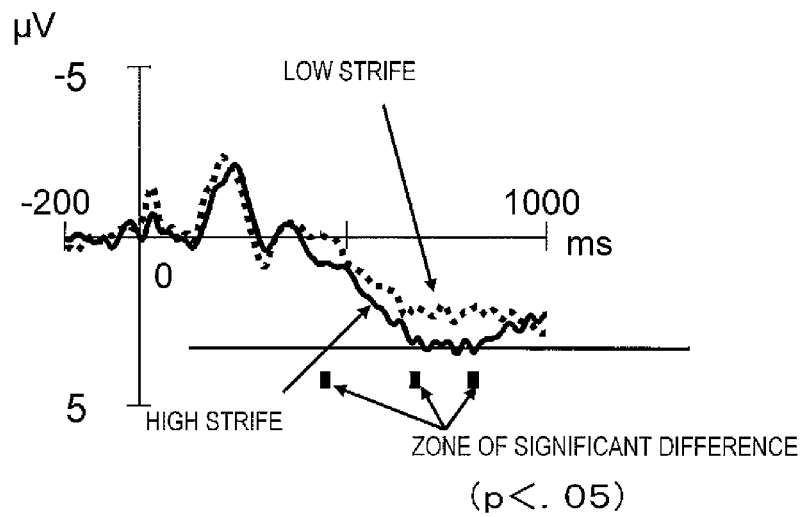
FIG. 7A is a diagram showing a waveform obtained, for each of high strife/low strife as labeled with a method according to an embodiment, by taking a total arithmetic mean of event-related potentials at the parietal (Pz) based on audio presentation as a starting point.

FIG. 7A shows waveforms of event-related potentials at the parietal (Pz), based on audio presentation as a starting point, where a total arithmetic means is taken for each of high strife/low strife as labeled by the aforementioned method. An arithmetic mean was taken based on the subjective evaluations concerning strife for respective blocks, under the six conditions in the above-described measurement experiment. In FIG. 7A, the horizontal axis represents time in units of ms, whereas the vertical axis represents potential in units of μV. As is clear from the scales shown in FIG. 7A, the lower direction in the graph corresponds to plus (positive), and the upper direction corresponds to minus (negative). In FIG. 7A, a broken line represents a total arithmetic mean waveform in the case of low strife, and a solid line represents a total arithmetic mean waveform in the case of high strife.

Figure 7B:
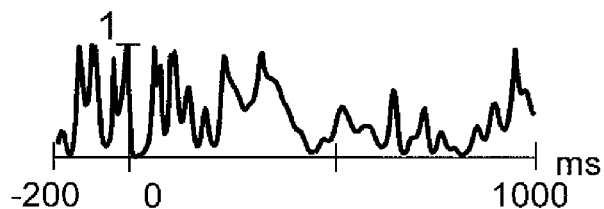
FIG. 7B is a diagram showing plotting of p values of t-test results at respective samplings.

It can be seen from FIG. 7A that positive components at a latency of 600 to 900 ms appear with a larger amplitude in the case of high strife (solid line) than in the case of low strife (broken line) in speech sound listening. The zone average potential from 600 to 900 ms for each subjective evaluation was: 1.99 μV in the case of low strife, and 2.73 μV in the case of high strife. As a result of t-testing the zone average potentials, there was a significant difference at the 10% level. FIG. 7B shows p values of t-test results at respective samplings. It can be seen from FIG. 7B that the p value is smaller in a time slot from about 600 to 900 ms, based on audio stimulation as a starting point, than in any other time slot. Therefore, there is a possibility that strife in speech sound listening is reflected in the positive potential at a latency of about 600 to 900 ms based on audio presentation as a starting point. A t-test conducted at every sampling between 0 ms and 1000 ms found the following time slots in which a significant difference due to a difference in subjective evaluation lasted for 15 ms or more: 420 to 445 ms; 655 to 670 ms; 730 to 745 ms; and 775 to 830 ms ($p<0.05$).

Figure 8:
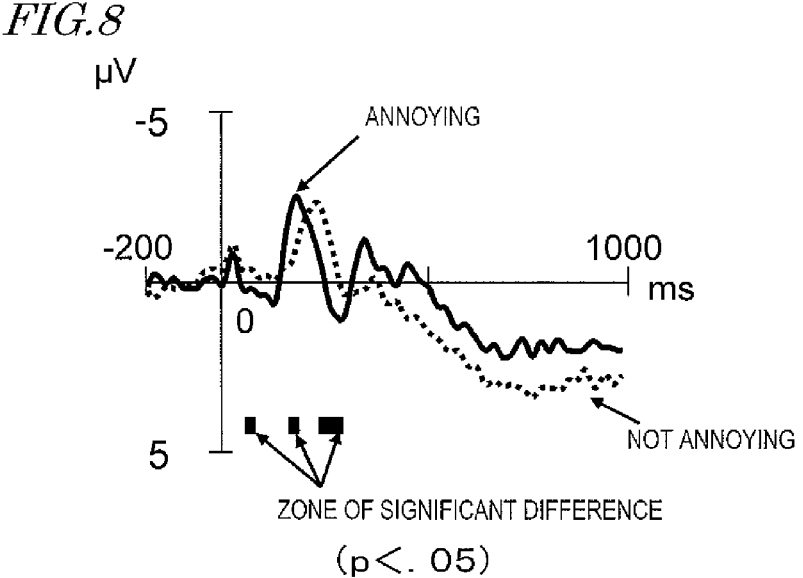
FIG. 8 is a diagram showing a waveform obtained, for each of "annoying"/"not annoying" labels, by taking a total arithmetic mean of event-related potentials at the parietal (Pz) based on audio stimulation as a starting point.

FIG. 8 shows waveforms of event-related potentials at the parietal (Pz), based on audio stimulation as a starting point, where a total arithmetic mean is taken for each of "annoying"/"not annoying" as labeled by the aforementioned method. An arithmetic mean was taken based on the subjective evaluations concerning annoyance for respective blocks, under the six conditions in the above-described measurement experiment. In FIG. 8, the horizontal axis represents time in units of ms, whereas the vertical axis represents potential in units of µV. As is clear from the scales shown in FIG. 8, similarly to FIG. 7A, the lower direction in the graph corresponds to plus (positive), and the upper direction corresponds to minus (negative). In FIG. 8, a solid line represents a total arithmetic mean waveform in the case of "annoying", and a broken line represents a total arithmetic mean waveform in the case of "not annoying".

It can be seen from FIG. 8 that a negative component (N1 component) which is induced at a latency of about 200 ms has a shorter latency in the case of "annoying" (solid line) than in the case of "not annoying" (broken line). The latency of the N1 component of each participant was 195 ms in the case of "annoying", and 240 ms in the case of "not annoying". As a result of t-testing the latencies, a significant difference was recognized ($p<0.05$). A zone average potential at a latency from 200 ms to 300 ms of each participant was 0.14 µV in the case of "annoying", and −1.38 µV in the case of "not annoying". As a result of t-testing the zone average potentials at latencies from 200 ms to 300 ms, the zone average potentials in the case of "annoying" were significantly larger ($p<0.05$). Therefore, it can be said that the latency of an N1 component based on audio presentation as a starting point and an average potential of a negative component at about 200 to 300 ms based on audio presentation as a starting point reflect annoyance, and can be used as an index of annoyance in speech sound listening. A t-test conducted at every sampling between 0 ms and 1000 ms found the following time slots in which a significant difference due to a difference in subjective evaluation lasted for 15 ms or more: 50 to 70 ms; 155 to 175 ms; 225 to 290 ms; and 920 to 935 ms.

3. Discussion

Thus, it became clear through the electroencephalogram measurement experiment that there are electroencephalogram components which respectively reflect strife and annoyance, as factors of comfortableness of speech sound listening. Specifically, it was found that strife is reflected in a positive potential having a peak at a latency of about 750 ms, and that annoyance is reflected in a negative potential having a peak at a latency of about 200 ms.

Concerning negative components, there have been reports that, when a pure tone is presented as a stimulation, an N1 component (a negative component at a latency of about 100 ms) increases in amplitude with an increase in the sound pressure of the stimulation sound (for example, Naatanen, R., & Picton, T. W. (1987). The N1 wave of the human electric and magnetic response to sound: a review and an analysis of the component structure. Psychophysiology, 24, 375-425).

However, since the amplitude of the N1 component changes depending not only on the sound pressure, but also on the rise and duration of the stimulation sound, the relationship between the sound pressure level and the negative component has not been clear in the case where a "speech sound", which undergoes changes in its rise, frequency, and power over time, is used as a stimulation. In addition, no difference that reflects a subjective report ("annoying"/"not annoying") of annoyance in audio stimulation listening has been known to occur in the N1 component.

Therefore, the fact that a negative component at a latency of about 200 ms increases in amplitude in a manner of reflecting a user's subjective perception concerning annoyance in speech sound listening ("annoying"/"not annoying") had never been clear before the electroencephalogram measurement experiment conducted by the inventors.

The aforementioned positive component at a latency of about 750 ms (FIG. 7) and the negative component at a latency of about 200 ms (FIG. 8) concerning different subjective evaluations of annoyance at the parietal (Pz) are distinguishable by a method of applying threshold processing to the peak amplitude levels in the relevant zone, a method of generating templates from typical waveforms of these components and calculating similarity levels with such templates, and so on. Note that the threshold values and templates may be those of a typical user as previously stored, or may be generated for each individual person.

In this experiment, arithmetic means were taken from the data of 13 participants in order to confirm the fact that components which reflect the confidence of aural distinction and the subjective perception concerning annoyance appear in an event-related potential based on a point of audio presentation as a starting point. However, depending on the method of characteristic amount extraction (e.g., wavelet transformation of the waveform) or the method of identification (e.g., support vector machine learning), identification of a positive component or a negative component is possible with no summations or only a small number of summations.

In the present specification, in order to define a component of an event-related potential, a point in time after the lapse of a predetermined time since a given point is expressed by referring to a "latency of about 750 ms", for example. This means possible inclusion of a range around the specific point of 750 ms in time. Generally speaking, there are 30 to 50 ms of differences (shifts) in event-related potential waveform between individuals, according to table 1 on p. 30 of "JISHOUKANRENDENI (ERP) MANYUARU—P300 WO CHUSHINNI—(or "Event-Related Potential (ERP) Manual—mainly concerning P300-"), edited by Kimitaka KAGA et al., Shinohara Shuppan Shinsha, 1995)". Therefore, the terms "about X ms" and "near X ms" mean that a breadth of 30 to 50 ms may exist before or after X ms (e.g., 300 ms±30 ms, 750 ms±50 ms).

Although the aforementioned "breadth of 30 ms to 50 ms" is a generic example of an individual difference in the P300 component, greater individual differences exist between users with respect to the aforementioned positive component at a latency of about 750 ms, which is later in latency than P300. Therefore, the aforementioned positive component is preferably treated as having a broader breadth, e.g., a breadth of about 100 ms to 150 ms on each of the earlier side and the later side. Accordingly, in the present embodiment, a "latency of about 750 ms" is meant to indicate a latency falling within the range from 600 ms to 900 ms.

Similarly, "near a latency of 200 ms" and "a latency of about 200 ms" may be construed as having a breadth of 30 ms to 50 ms on each of the earlier side and the later side of the latency of 200 ms, or even having a slightly greater breadth, e.g., a breadth of 50 ms to 100 ms on each of the earlier side and the later side. In other words, in the present embodiment, a "latency of about 200 ms" may be construed as a latency of no less than 100 ms and no more than 300 ms.

Thus, the inventors have found through their electroencephalogram measurement experiment that, in an event-related potential based on the point of audio presentation as a starting point: (1) a positive component at a latency of about 750 ms reflects strife in speech sound listening; and that (2) a negative component at a latency of about 200 ms reflects annoyance. Strife and annoyance are the two comfortableness factors to be assessed in speech sound listening that have been identified by the inventors.

Therefore, based on the assessment results of strife and annoyance together, which are obtained by using as an index an event-related potential in response to an audio stimulation, a comfortableness assessment of speech sound listening can be realized.

FIG. 9A shows correspondence between the presence or absence of the positive component/negative component and strife/annoyance determinations, as compiled by the inventors. Based on the presence or absence of the positive component, if the positive component is absent (i.e., the amplitude of the positive component is equal to or smaller than a threshold value), a low strife determination is made; if the positive component is present (i.e., the amplitude of the positive component is greater than the threshold value), a high strife determination is made. Moreover, based on the presence or absence of the negative component, if the negative component is absent (i.e., the latency of the negative component is equal to or greater than a threshold value), a "not annoying" determination is made; if the negative component is present (i.e., the latency of the negative component is shorter than the threshold value), an "annoying" determination is made.

Note that a "positive component" would generally mean a potential which is greater than 0 μV. However, in the context of the present specification, it is not a requirement for a "positive component" to be absolutely positive (i.e., greater than 0 μV). In the present specification, the presence or absence of a "positive component" is identified in order to identify a high or low confidence of aural distinction; so long as a significant highness or lowness of confidence of aural distinction is distinguishable, it does not matter if the zone average potential, etc., is 0 μV or less.

Note that a "negative component" would generally mean a potential which is smaller than 0 μV, however long or short its latency may be. However, in the present specification, in order to distinguish whether the user has felt "annoyed" or not, the case where the latency is equal to or shorter than a predetermined threshold value is defined to indicate that "the negative component is present", and the case where the latency is longer than the predetermined threshold value is defined to indicate that "the negative component is absent". Specific examples of the threshold value will be described later.

FIG. 9B shows correspondence between the presence or absence of a positive component and a negative component and acoustic aiding process assessments. Cell (A) is a case where both of the positive component and the negative component are present. In this case, it is estimated that the gain adjustment has been made for a less-than-optimum frequency, or that the amount of gain adjustment for each frequency is excessive. Cell (B) is a case where the positive component is present but the negative component is absent. In this case, it is estimated that aural distinction is possible with strife but the need for strife makes it difficult for the hearing aid to be worn on a daily basis. Cell (C) is a case where the positive component is absent, but the negative component is present. In this case, it is estimated that although strife is not needed for speech sound listening, the overall amplification is excessive. Cell (D) is a case where neither the positive component nor the negative component is present. In this case, it is estimated that the acoustic aiding process is suitable, such that user is able to aurally distinguish speech sounds in comfort.

Thus, strife and annoyance are determined based on the presence or absence of the positive component and the negative component, whereby comfortableness of speech sound listening is assessed. As a result, even under the same intelligibility, it is possible to determine whether the user needs strife or not, and whether the user is feeling "annoyed" or not, in speech sound listening. Accordingly, the amount of gain adjustment may be universally increased (when the result corresponds to cell (B)), or the amount of gain adjustment may be universally decreased (when the result corresponds to cell (C)), for example, thus arriving at a specific fitting procedure for achieving an improved comfortableness of speech sound listening.

Hereinafter, a comfortableness assessment system according to an embodiment of the present disclosure will be described. The comfortableness assessment system sequentially presents monosyllabic speech sounds in the form of audios, and determines strife and annoyance in speech sound listening, by relying on the presence or absence of a positive component at a latency of about 750 ms and a negative component at a latency of about 200 ms in an event-related potential based on the point of audio presentation as a starting point, thus realizing a comfortableness assessment. This is unprecedentedly realized by the findings of the inventors.

4. Embodiment 1

Hereinafter, the comfortableness assessment system will be first described in outline. Thereafter, the construction and operation of a comfortableness assessment system including a speech sound listening comfortableness assessment apparatus will be described.

The comfortableness assessment system of the present embodiment sequentially presents audios, and an event-related potential is measured based on each point of audio presentation as a starting point. Then, a positive component at a latency of about 750 ms and a negative component at a latency of about 200 ms are detected, and strife and annoyance serving as the factors of comfortableness of speech sound listening are determined.

In the present embodiment, a probe electrode was placed at the parietal (Pz), and a reference electrode was placed at the right or left mastoid, and an electroencephalogram was measured as a potential difference between the probe electrode and the reference electrode. Note that the levels and polarities of the characteristic components of the event-related potential may vary depending on the position at which the electrode for electroencephalogram measurement is attached, and the manner in which the reference electrode and the probe electrode are set. However, based on the following description, those skilled in the art would be able to detect a characteristic component of the event-related potential and make a speech sound intelligibility assessment by making appropriate modifications depending on the specific reference electrode and probe electrode. Any such variant is encompassed within the present disclosure.

In the above description of the electroencephalogram measurement experiment, the relative strength of the frequency gain is experimentally varied for participants with normal hearing, thus simulating the hearing of a person suffering from hypacusia. However, when conducting an assessment for a person suffering from hypacusia, there is no particular need to present speech sounds that are difficult to aurally distinguish. In the present embodiment, it is assumed that audios are presented whose gain for each frequency has been optimally adjusted based on a fitting method from audiograms of people suffering from hypacusia that were measured in advance.

Figure 10:
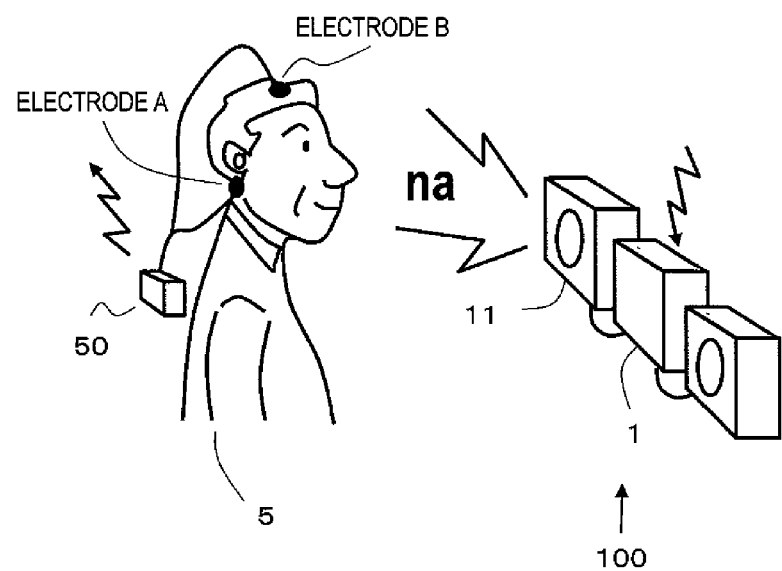
FIG. 10 is a diagram showing a construction and an environment of use for a comfortableness assessment system 100 according to the present embodiment.

FIG. 10 shows a construction and an environment of use for a comfortableness assessment system 100 of the present embodiment. The comfortableness assessment system 100 is exemplified so as to correspond to a system construction of Embodiment 1 described later. Note that the "comfortableness assessment system" may also be referred to as an "assessment system of speech sound listening", which similarly applies to subsequent Embodiments 2 and 3.

The comfortableness assessment system 100 includes a speech sound listening comfortableness assessment apparatus 1, an audio output section 11, and a biological signal measurement section 50. The biological signal measurement section 50 is connected to at least two electrodes A and B. Electrode A is attached at a mastoid of the user 5, whereas electrode B is attached on the scalp at the parietal (so-called Pz) of the user 5.

The comfortableness assessment system 100 presents a monosyllabic speech sound to the user 5 in the form of an audio at a certain sound pressure, and determines the presence or absence of a positive component at a latency of about 750 ms in an electroencephalogram (event-related potential) from the user 5 which is measured based on the point of audio presentation as a starting point and the presence or absence of a negative component at a latency of about 200 ms. Then, based on the presented audio and the presence or absence of the positive component and the negative component, it is determined whether user was striving or not and whether the user was feeling annoyed or not in speech sound listening, respectively.

An electroencephalogram from the user 5 is acquired by the biological signal measurement section 50 based on a potential difference between electrode A and electrode B. The biological signal measurement section 50 sends information corresponding to the potential difference (electroencephalogram signal) to the speech sound listening comfortableness assessment apparatus 1 in a wireless or wired manner. FIG. 10 illustrates an example where the biological signal measurement section 50 wirelessly sends this information to the speech sound listening comfortableness assessment apparatus 1.

The speech sound listening comfortableness assessment apparatus 1 performs sound pressure control of the audio used for comfortableness assessment of speech sound listening, controls presentation timing of the audio, and presents an audio via the audio output section 11 (e.g., loudspeakers) to the user 5.

Figure 11:
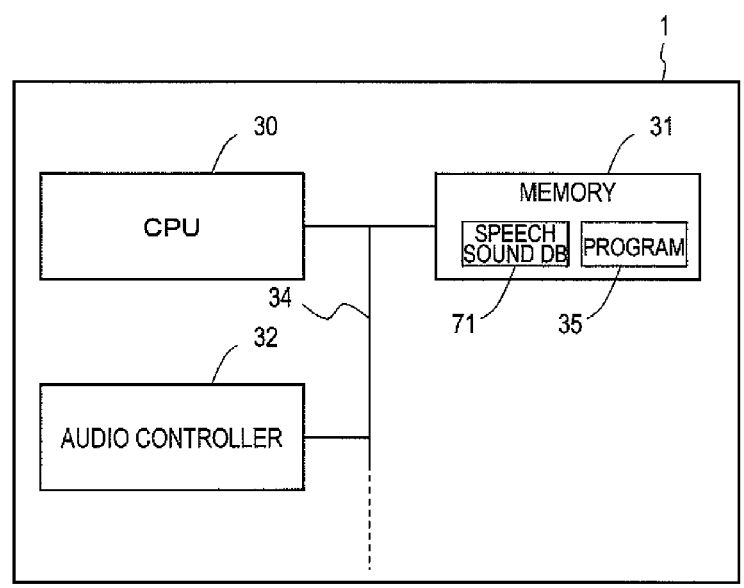
FIG. 11 is a diagram showing the hardware construction of a speech sound listening comfortableness assessment apparatus 1 of Embodiment 1.

FIG. 11 shows a hardware construction of the speech sound listening comfortableness assessment apparatus 1 according to the present embodiment. The speech sound listening comfortableness assessment apparatus 1 includes a CPU 30, a memory 31, and an audio controller 32. These elements are interconnected via a bus 34 so that data exchange among them is possible.

The CPU 30 executes a computer program 35 which is stored in the memory 31. A processing procedure as illustrated by a subsequently-described flowchart is described in the computer program 35. In accordance with the computer program 35, the speech sound listening comfortableness assessment apparatus 1 performs a process of controlling the entire comfortableness assessment system 100, by utilizing a speech sound database (DB) 71 which is also stored in the same memory 31. This process will be described in detail later.

In accordance with instructions from the CPU 30, the audio controller 32 generates an audio to be presented, and outputs the generated audio signal to the audio output section 11 at a designated sound pressure.

Note that the speech sound listening comfortableness assessment apparatus 1 may be implemented as a piece of hardware (e.g., a DSP) consisting of a semiconductor circuit having a computer program incorporated therein. Such a DSP can realize all functions of the aforementioned CPU 30, memory 31, and audio controller 32 on a single integrated circuit.

The aforementioned computer program 35 may be distributed on the market in the form of a product recorded on a storage medium such as a CD-ROM, or transmitted through telecommunication lines such as the Internet. Upon reading the computer program 35, a device having the hardware shown in FIG. 11 (e.g., a PC) is able to function as the speech sound listening comfortableness assessment apparatus according to the present embodiment. Note that the speech sound DB 71 does not need to be stored in the memory 31, but may be stored on a hard disk (not shown) which is connected to the bus 34.

Figure 12:
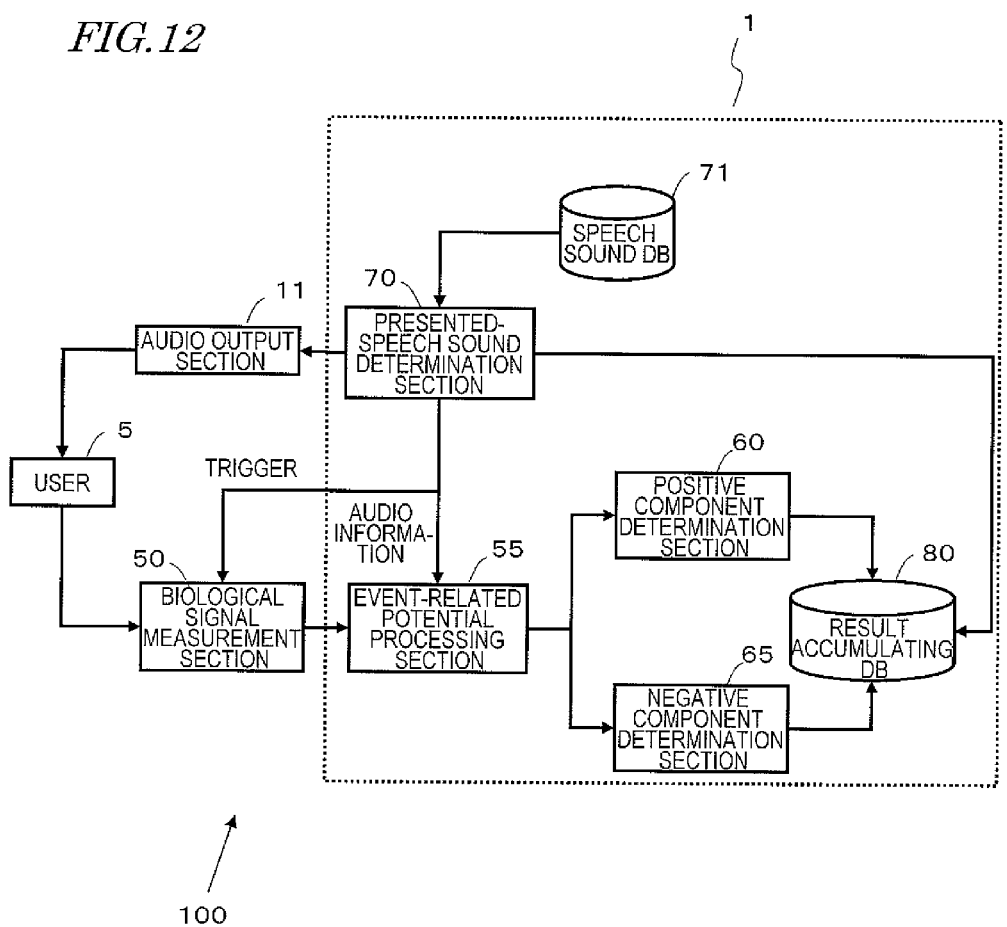
FIG. 12 is a diagram showing the functional block construction of the comfortableness assessment system 100 of Embodiment 1.

FIG. 12 shows a functional block construction of the comfortableness assessment system 100 of the present embodiment. The comfortableness assessment system 100 includes the audio output section 11, the biological signal measurement section 50, and the speech sound listening comfortableness assessment apparatus 1. FIG. 12 also shows detailed functional blocks of the speech sound listening comfortableness assessment apparatus 1. Specifically, the speech sound listening comfortableness assessment apparatus 1 includes an event-related potential processing section 55, a positive component determination section 60, a negative component determination section 65, a presented-speech sound determination section 70, a speech sound DB 71, and a result accumulating DB 80. The user 5 block is illustrated for ease of explanation.

The respective functional blocks (except the speech sound DB 71) of the speech sound listening comfortableness assessment apparatus 1 correspond to functions which are realized by the CPU 30, the memory 31, and the audio controller 32 as a whole upon executing the program which has been described in conjunction with FIG. 11.

Figure 13:
FIG. 13 is a diagram showing an example of a speech sound DB 71 in the case where 20 speech sounds of the 67S list are used as test speech sounds.

The speech sound DB 71 is a database of speech sounds which is provided for performing a comfortableness assessment of speech sound listening. FIG. 13 shows an exemplary speech sound DB 71 in the case where 20 speech sounds of the 67S list are to be used as test speech sounds.

In the speech sound DB 71 shown in FIG. 13, audio files to be presented, consonant labels, and grouped data based on likelihood of confusion (how likely confusion will occur) are associated. As for the stored audios, it is assumed that the gain adjustment (acoustic aiding process) for each frequency has been completed based on a fitting theory from audiograms of people suffering from hypacusia that were measured in advance. The types of speech sounds to be stored may be the 50 sounds of the 57S list, instead of the 20 speech sounds of the 67S list. The consonant labels are utilized when assessing a consonant that incurs a high strife or annoyance by the user 5. The grouped data is utilized when assessing the group that incurs a high strife or annoyance by the user 5. The grouping may be a rough category, a medium category, and a fine category, for example.

The rough category concerns categorization as to vowels, unvoiced consonants, and voiced consonants, which are respectively represented as 0, 1, and 2. The medium category defines sub-categorization among unvoiced consonants and among voiced consonants. The unvoiced consonants can be categorized into the sa-row (medium category: 1) and the ta-/ka-/ha-rows (medium category: 2), whereas the voiced consonants can be categorized into the ra-/ya-/wa-rows (medium category: 1) and the na-/ma-/ga-/za-/da-/ba-rows (medium category: 2). The fine category can be divided into the na-/ma-rows (fine category: 1) and the za-/ga-/da-/ba-rows (fine category: 2), for example. As for likelihood of confusion, the inventors relied on "HOCHOKI FITTINGU NO KANGAEKATA (or "Concept of Hearing Aid Fitting") (Kazuoki KODERA, Shindan To Chiryosha, 1999, p. 172).

FIG. 12 is again referred to. The presented-speech sound determination section 70 determines which speech sound is to be presented at what sound pressure level, by referring to the speech sound DB 71. The speech sounds for presentation may be selected and determined by random order, for example. It is assumed that the sound pressure levels of the speech sounds for presentation are sound pressure levels which are obtained after applying an acoustic aiding process to audios of 55 dB SPL, 65 dB SPL, 75 dB SPL, and 85 dB SPL in a speech sound intelligibility curve measurement. The sound pressure levels may sequentially varied from smaller sound pressure levels to larger sound pressure levels, or in the opposite order of this. Alternatively, sound pressure levels may be selected by random order.

In accordance with the point of audio presentation, the presented-speech sound determination section 70 outputs a trigger to the biological signal measurement section 50, and sends the actual audio to be presented to the event-related potential processing section 55.

The audio output section 11 reproduces the monosyllabic audio which is determined by the presented-speech sound determination section 70, thereby presenting it to the user 5.

The biological signal measurement section 50, which is an electroencephalograph for measuring a biological signal of the user 5, measures an electroencephalogram as the biological signal. Then, the biological signal measurement section 50 cuts out an event-related potential of the electroencephalogram in a predetermined zone (e.g., a zone from −200 ms to 1000 ms) based on the trigger received from the presented-speech sound determination section 70 as a starting point, and sends the waveform data (electroencephalogram data) thereof to the event-related potential processing section 55. It is assumed that the user has already put on the electroencephalograph. The electrode for electroencephalogram measurement is attached at the parietal Pz, for example.

The event-related potential processing section 55 receives event-related potentials from the biological signal measurement section 50, and in accordance with the actual audio to be presented that is received from the presented-speech sound determination section 70, performs an arithmetic mean calculation of the event-related potentials. The event-related potential processing section 55 may only select the event-related potentials corresponding to audio presentations of the same speech sound, thus performing an arithmetic mean calculation of the event-related potentials for each speech sound type, for example. Taking an arithmetic mean only of the event-related potentials for the same speech sound makes possible a comfortableness assessment for each speech sound. The arithmetic mean may be performed for selected speech sounds that share the same consonant, or performed for each rough category, medium category, or fine category of the grouping shown in FIG. 13. Taking an arithmetic mean of speech sounds sharing the same consonant enables strife and annoyance assessments in speech sound listening with respect to each consonant type. Taking an arithmetic mean for each group enables an assessment of aural distinction as to the group, e.g., "between voiced consonants and unvoiced consonants, higher strife is made for the unvoiced consonants". From a consonant-by-consonant or group-by-group arithmetic mean, a summed waveform is obtained with more than a few summations being made. Moreover, irrespective of the speech sound type, event-related potentials for audio presentations with the same sound pressure may be selected for an arithmetic mean, for example. Taking an arithmetic mean for the same sound pressure enables a comfortableness assessment for each sound pressure.

The event-related potential processing section 55 sends the electroencephalogram data which has been obtained by perform an arithmetic mean calculation over a predetermined number of times for each speech sound to the positive component determination section 60 and to the negative component determination section 65. Depending on the destination of electroencephalogram data, different processes may be performed for the event-related potential. For example, the number of times over which to perform an arithmetic mean calculation may be varied depending on the destination, or one of two kinds of filtering processes with different cutoff frequencies may be selected depending on the destination when performing a filtering process for the event-related potential waveform. As is also clear from FIG. 7 and FIG. 8, the negative component at a latency of about 200 ms differs in frequency from the positive component at a latency of about 750 ms, the negative component being of a higher frequency. Electroencephalogram data with a higher signal/noise ratio can be obtained by applying a different filtering process depending on the destination.

The positive component determination section 60 and the negative component determination section 65 receive the electroencephalogram data from the event-related potential processing section 55 and perform different analyses as will be described later.

Based on the electroencephalogram data received from the event-related potential processing section 55, the positive component determination section 60 determines the presence or absence of a positive component at a latency of about 750 ms. The method of identifying the presence or absence of the positive component is as follows.

For example, the positive component determination section 60 compares the maximum amplitude at a latency from 600 ms to 900 ms, or a zone average potential at a latency from 600 ms to 900 ms, against a predetermined threshold value. The predetermined threshold value when using a zone average potential may be 2.36 μV, i.e., a median between the zone average potentials for "high strife" and "low strife" obtained in the aforementioned experiment, this serving as a threshold value for the presence or absence of the positive component of a generic user. Then, if the zone average potential is greater than the threshold value, the positive component determination section 60 may identify the case as "the positive component is present", or if the zone average potential is smaller than the threshold value, the positive component determination section 60 may identify the case as "the positive component is absent".

Alternatively, by relying on a similarity level (e.g., a correlation coefficient) with a predetermined template which is generated from the waveform of a typical positive component signal at a latency of about 750 ms, the positive component determination section 60 may determine similarity. If similarity can be asserted, the positive component determination section 60 may identify the case as "the positive component is present"; if similar cannot be asserted, the positive component determination section 60 may identify the case as "the positive component is absent". The predetermined template may be calculated or generated from a previously-acquired positive component waveform of a generic user.

The negative component determination section 65 identifies the presence or absence of a negative component at a latency of about 200 ms in the electroencephalogram data received from the event-related potential processing section 55. For example, the negative component determination section 65 compares the latency of a negative potential peak at a latency of from 100 ms to 300 ms against a predetermined threshold value. Then, if the peak latency of the negative potential is shorter than the predetermined threshold value, the negative component determination section 65 may identify the case as "the negative component is present"; if the peak latency is equal to or greater than the predetermined threshold value, the negative component determination section may identify the case as "the negative component is absent".

For example, the "predetermined threshold value" may be 218 ms, which is a median of the latency of the negative component concerning "annoying"/"not annoying" that was obtained in the aforementioned experiment as a threshold value for the presence or absence of the negative component of a generic user. Alternatively, by relying on a similarity level ((e.g., correlation coefficient) with a predetermined template which is generated from the waveform of a typical negative component signal at a latency of about 200 ms, the negative component determination section 65 may determine similarity. If similarity can be asserted, the negative component determination section 65 may identify the case as "the negative component is present"; if similar cannot be asserted, the negative component determination section 65 may identify the case as "the negative component is absent". The predetermined threshold value or template may be calculated or generated from a previously-acquired negative component waveform of a generic user.

The result accumulating DB 80 receives information of the presented audio from the presented-speech sound determination section 70. Moreover, the result accumulating DB 80 receives speech-sound-by-speech-sound information of the presence or absence of the positive component from the positive component determination section 60, and speech-sound-by-speech-sound information of the presence or absence of the negative component from the negative component determination section 65. Then, with respect to each speech sound and each sound pressure level of the presented audio, for example, the result accumulating DB 80 accumulates information of the received results of strife and annoyance determinations.

Note that, upon determining that the positive component is present, the positive component determination section 60 may output an assessment result that the user is listening to the speech sound with strife, and upon determining that the positive component is absent, output an assessment result that the user is hearing the speech sound without strife.

In addition to the dichotomic determination of either "with strife" or "without strife", a strife level that corresponds to the amplitude or zone average potential of the positive component may also be included in the result of strife determination. In this case, the positive component determination section 60 has a plurality of threshold values or templates that are associated with strife levels.

For example, consider a case where the threshold value decreases in order from a third threshold value to a fourth threshold value (i.e., the fourth threshold value being smaller than the third threshold value). If the amplitude value of the positive component is equal to or greater than the third threshold value, it may be determined that there is large strife. If the amplitude value of the positive component is equal to or greater than the fourth threshold value and yet smaller than the third threshold value, it may be determined that there is medium strife. If the amplitude value of the positive component is smaller than the fourth threshold value, it may be determined that there is little strife. Moreover, an amplitude value or zone average potential value of the positive component may be used as a result of determination.

The same also applies to the result of annoyance determination by the negative component determination section 65.

Upon determining that the negative component is present, the negative component determination section 65 may output an assessment result that the user is annoyed by the speech sound, and upon determining that the negative component is absent, the negative component determination section 65 may output an assessment result that the user is not annoyed by the speech sound.

Moreover, in addition to the two values of "annoying" and "not annoying", an annoyance level that corresponds to the latency of the negative component may also be included in the result of determination by the negative component determination section 65. In this case, the negative component determination section 65 has a plurality of threshold values or templates, similarly to the positive component determination section 60.

Figure 14:
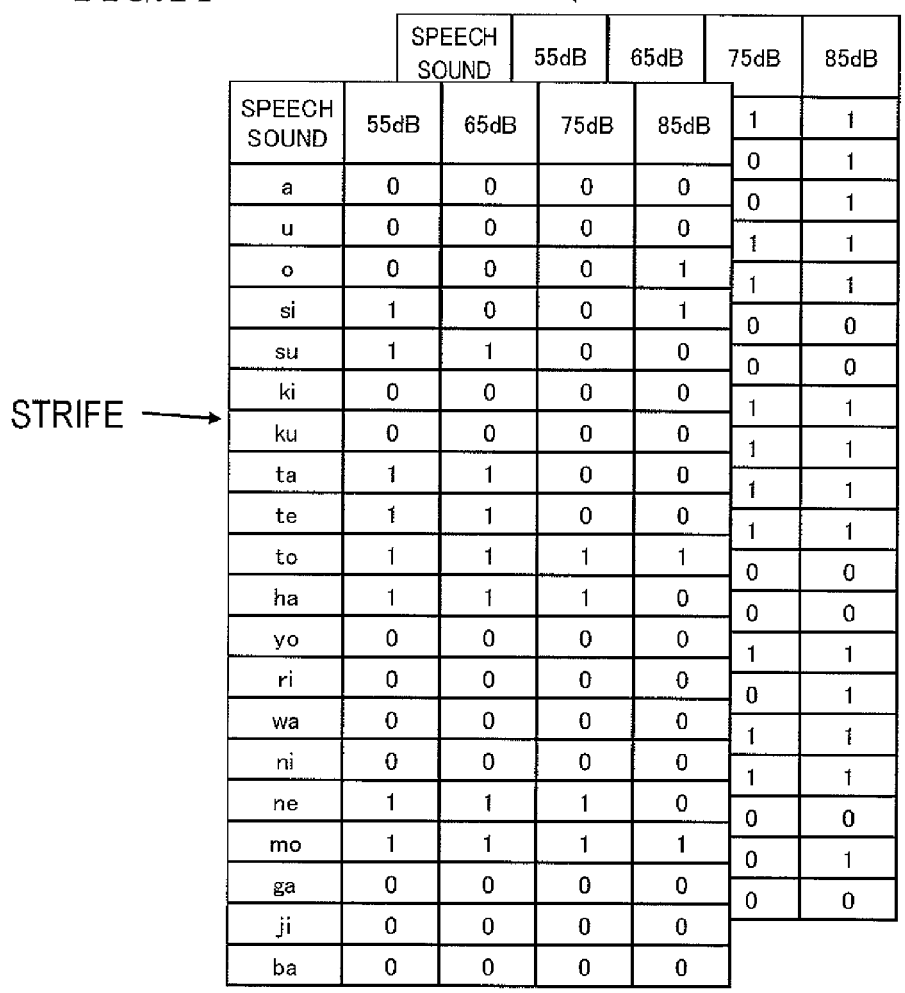
FIG. 14 is a diagram showing an example of data accumulation in a result accumulating DB 80.

FIG. 14 shows an example of data accumulation in the result accumulating DB 80. FIG. 14 illustrates an example where strife and annoyance information is accumulated with respect to each speech sound and each sound pressure level. For example, in FIG. 14, "1" denotes a case where the positive component determination section 60 or the negative component determination section 65 determines that the positive component or the negative component is present, and "0" denotes a case where the positive component determination section 60 or the negative component determination section 65 determines that the positive component or the negative component is absent.

As a comfortableness assessment method based on the results of strife and annoyance determinations, for example, a proportion of the speech sounds producing the determination that the positive component is absent and a proportion of the speech sounds producing the determination that the negative component is absent may be calculated with respect to each sound pressure level, and averaged to provide a result of comfortableness assessment. Alternatively, with respect to at least one sound pressure level, a proportion of the speech sounds producing the determination that the positive component is absent and a proportion of the speech sounds producing the determination that the negative component is absent may be calculated, and a result of comfortableness assessment may be generated by utilizing these calculation results. Instead of a proportion of speech sounds, a proportion of consonants or groups concerning probability of confusion may be utilized to produce a result of comfortableness assessment.

The process of comfortableness assessment may be performed by the result accumulating DB 80, for example. In this case, the result accumulating DB 80 is not a mere storage medium; in addition to being a storage medium, it has a function of enabling a search and extraction from the information accumulated in the storage medium, and so on. Such functions may be realized by a piece of hardware or software functioning as a database server, for example (neither is shown). This database server may perform the aforementioned calculation process.

Figure 15B:
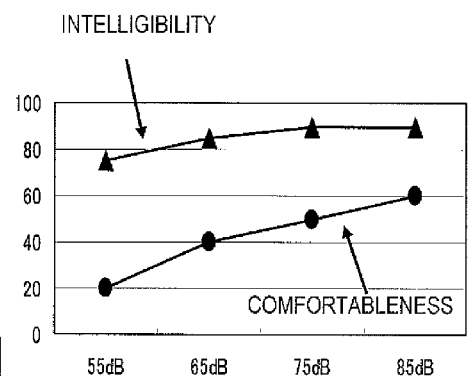
FIGS. 15A to 15C are diagrams showing measurement results of speech sound intelligibility curves (conventional assessment), and in addition to the conventional assessment, exemplary results of a comfortableness assessment in speech sound listening according to Embodiment 1.
Figure 15A:
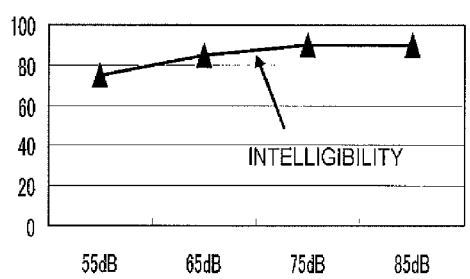
Figure 15C:
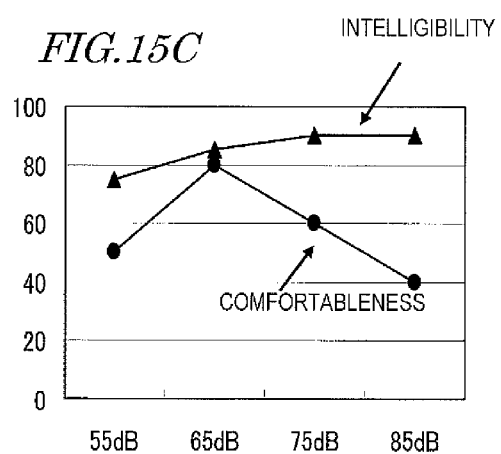

FIG. 15A to 15C show measurement results of speech sound intelligibility curves (conventional assessment), and in addition to the conventional assessment, exemplary results of a comfortableness assessment in speech sound listening according to the present embodiment. FIG. 15A shows an example where only speech sound intelligibility with respect to each sound pressure level of the presented audio is assessed when wearing a hearing aid. This example illustrates an assessment result which is obtained by a conventional assessment technique. In this example, the intelligibility is assessed to be 80% or more at a sound pressure level of 65 dB SPL or more. Therefore, if the speech sound intelligibility is improved as compared to when not wearing a hearing aid (not shown in FIG. 15), a hearing aid suitability test would determine this case to be suitable.

FIGS. 15B and 15C show exemplary assessment results where a comfortableness assessment based on strife and annoyance determination according to the present embodiment is employed in addition to the result of speech sound intelligibility curve measurement when wearing a hearing aid as shown in FIG. 15A. It is assumed that the speech sound intelligibility curve has been separately measured by a conventional method which involves oral explanation, key inputting, or the like.

In FIGS. 15B and 15C, although the speech sound intelligibility curves are identical, results of comfortableness assessment are quite different. For example, in FIG. 15B, the overall comfortableness is low, particularly at 55 dB. This leads to an assessment that the overall sound pressure was low, although hearing would be possible with strife. In FIG. 15C, for example, the overall comfortableness is high, but the comfortableness is low at a high sound pressure level. This leads to an assessment that, although the acoustic aiding process is appropriate at a sound pressure near 65 dB SPL, annoyance is felt at a sound pressure level as high as 85 dB SPL. These assessments are unprecedentedly obtained by assessing comfortableness of speech sound listening based on the two factors of strife and annoyance. Such assessments permit proposals of specific fitting procedures to be made, e.g., universally increasing the amount of gain adjustment in the case of FIG. 15B, or employing enhanced compression in non-linear amplification in the case of FIG. 15C.

Although FIGS. 15B and 15C illustrate comfortableness only when wearing a hearing aid, comfortableness may be assessed also when not wearing a hearing aid (naked ear), and a comfortableness comparison may be made between when not wearing a hearing aid and when wearing a hearing aid.

Next, with reference to FIG. 16, a processing procedure performed by the comfortableness assessment system 100 of FIG. 12 will be described.

Figure 16:
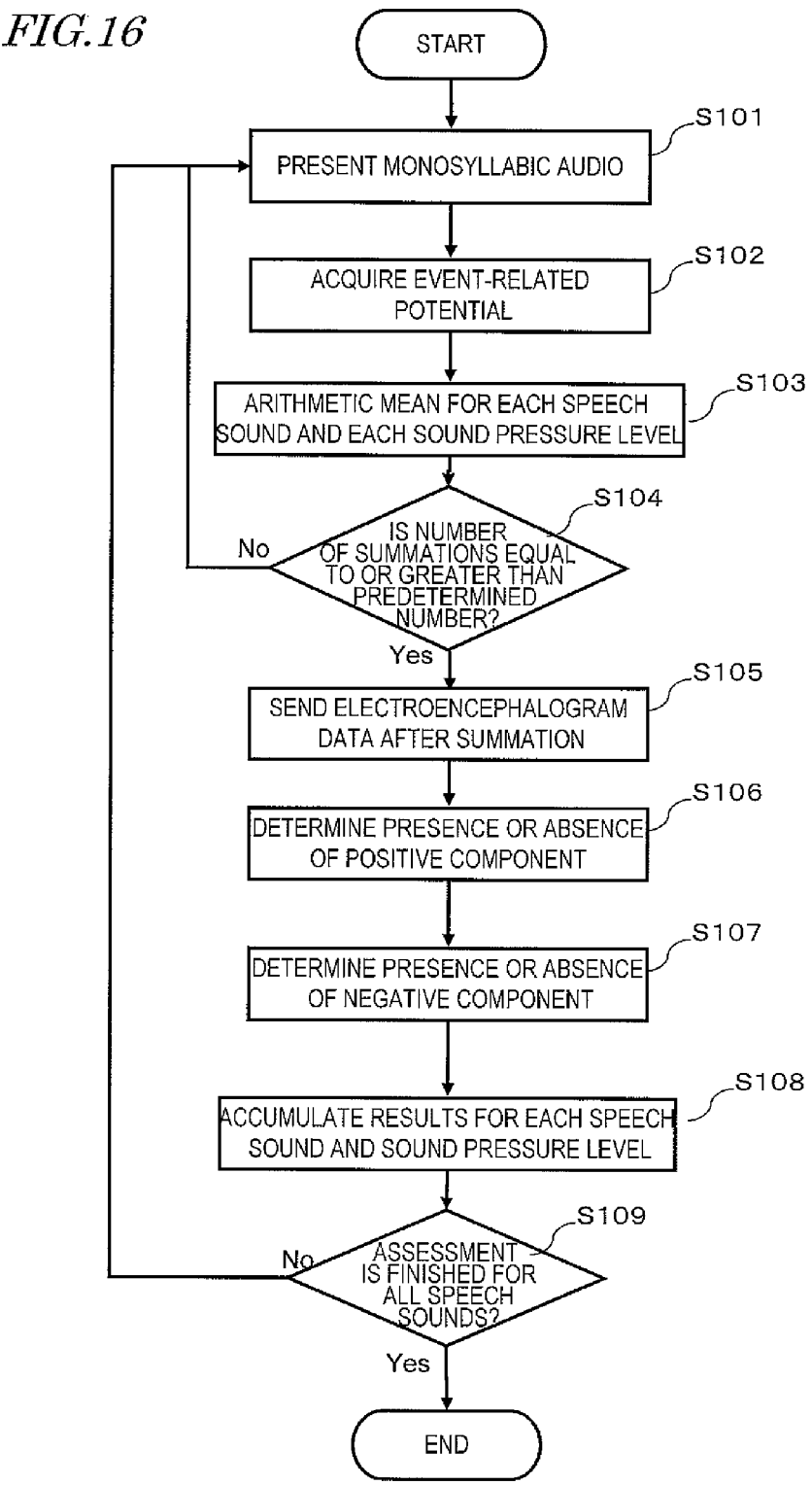
FIG. 16 is a flowchart showing a procedure of processing which is performed in the comfortableness assessment system 100.

FIG. 16 is a flowchart showing a procedure of processing performed by the comfortableness assessment system 100.

At step S101, by referring to the speech sound DB 71, the presented-speech sound determination section 70 determines a monosyllabic speech sound to be presented and a sound pressure level. The audio output section 11 presents the speech sound to the user 5 at the determined sound pressure level. The presented-speech sound determination section 70 sends a trigger to the biological signal measurement section 50, and sends audio information concerning the presented speech sound to the event-related potential processing section 55. The speech sound to be presented may be randomly selected from the speech sound DB 71, or a speech sound of a particular consonant or a group may be exclusively selected. The sound pressure level of the speech sound for presentation may be, for example, sound pressure levels which are obtained after applying an acoustic aiding process to audios of 55 dB SPL, 65 dB SPL, 75 dB SPL, and 85 dB SPL in a speech sound intelligibility curve measurement. The sound pressure levels of presentation may sequentially varied from smaller sound pressure levels to larger sound pressure levels, or in the opposite order of this. Alternatively, sound pressure levels may be selected by random order.

At step S102, upon receiving the trigger from the presented-speech sound determination section 70, the biological signal measurement section 50 cuts out an event-related potential from e.g. −200 ms to 1000 ms from the measured electroencephalogram, based on the trigger as a starting point. Then, an average potential from e.g. −200 ms to 0 ms is determined, and the resultant event-related potential is subjected to baseline correction so that this average potential becomes 0 μV.

At step S103, based on the information of the presented speech sound which is received from the presented-speech sound determination section 70, the event-related potential processing section 55 takes an arithmetic mean of the event-related potential cut out at step S102 with respect to each speech sound and each sound pressure level. Although an arithmetic mean calculation is performed with respect to each speech sound and each sound pressure level in the present embodiment, it is not necessary that the arithmetic mean calculation be performed with respect to each speech sound. For example, it may be performed with respect to each speech sound type (e.g., for each consonant or for each group of speech sounds), or with respect to each sound pressure level of presentation. In other words, in the case where each speech sound is classified based on at least one of the speech sound type and the sound pressure level of presentation, the event-related potential processing section 55 may take an arithmetic mean of event-related potentials of electroencephalogram signals which are obtained when speech sounds belonging to the same classification are presented.

At step S104, the event-related potential processing section 55 determines whether the number of summations for the event-related potential with respect to the speech sound presented at step S101 has reached a predetermined number of summations or not. If the number of summations is less than the predetermined number of times, the process returns to step S101 to repeat audio presentation. If the number of summations is equal to or greater than the predetermined number of times, the process proceeds to step S105. The number of summations may be 20 times, for example. Note that "20 times" is a mere example, although it is a number of summations which is frequently adopted in fields where event-related potentials are to be measured.

At step S105, the event-related potential processing section 55 sends the electroencephalogram data obtained by performing an arithmetic mean calculation over a predetermined number of times to the positive component determination section 60 and the negative component determination section 65.

At step S106, the positive component determination section 60 determines whether a positive component is present at a latency of about 750 ms in the electroencephalogram data. Identification of the positive component may be performed through comparison against a predetermined threshold value or comparison against a template, as mentioned above.

At step S107, the negative component determination section 65 determines whether a negative component is present at a latency of about 200 ms in the electroencephalogram data. Identification of the negative component may be performed through threshold comparison of the latency of a predetermined negative component, or through comparison against a template, as mentioned above.

At step S108, with respect to each speech sound and each sound pressure level presented at step S101, the result accumulating DB 80 accumulates the information received from the positive component determination section 60 concerning the presence or absence of the positive component at a latency of about 750 ms, and the information received from the negative component determination section 65 concerning the presence or absence of the negative component at a latency of about 200 ms.

At step S109, the presented-speech sound determination section 70 determines whether stimulation presentation has been completed for all of the speech sounds and sound pressure levels to be subjected to an assessment of comfortableness of speech sound listening. If it is not completed, the process returns to step S101; if it is completed, the comfortableness assessment of speech sound listening is ended.

From the comfortableness assessment results based on the factors of strife and annoyance, which are accumulated in the result accumulating DB 80 with respect to each speech sound and each sound pressure level, proposals of more specific fitting procedures can be made. For example, when the overall comfortableness is low, particularly at 55 dB, as shown in FIG. 15B, the amount of gain adjustment may be universally increased. Moreover, when the overall comfortableness is high but is low at higher sound pressure levels as shown in FIG. 15C, an enhanced compression may be employed in non-linear amplification.

In the present embodiment, on the premise of presenting a monosyllabic speech sound in the form of an audio, a comfortableness of speech sound listening is assessed through a process which utilizes a positive component at a latency of about 750 ms, and a negative component at a latency of about 200 ms, of an event-related potential based on the point of audio presentation as a starting point. Through the above process, in speech sound listening, a determination can be made as to how hard a user strived (strife) and how annoyed the user was (annoyance). This means that suitability of an acoustic aiding process can be assessed from the perspective of comfortableness of speech sound listening, which is distinct from speech sound intelligibility. Since acoustic aiding process assessments are possible from the perspective of comfortableness, an acoustic aiding process which is highly comfortable and not inducing aural fatigue can be realized.

Note that, as shown in FIG. 11, the speech sound listening comfortableness assessment apparatus 1 in the present embodiment is realized with a construction which permits downsizing and which employs generic hardware. By constructing the comfortableness assessment apparatus 1 in a portable size and weight that allows the user to carry it with himself or herself, it becomes possible to assess a comfortableness of speech sound listening in an acoustic environment in which the user actually uses a hearing aid. Although the audio output section 11 is illustrated as a speaker set in FIG. 10, the audio output section 11 may instead be headphones. Use of headphones facilitates transportation, thus enabling an assessment of a comfortableness of speech sound listening in an environment in which the user uses them.

The present embodiment has been illustrated based on assessments for the Japanese language. However, it may be English or Chinese so long as the speech sounds are monosyllabic. In the case of English, for example, monosyllabic words may be presented, and an evaluation may be made on a word-by-word basis. FIG. 17 shows an exemplary result of assessing strife and annoyance for different monosyllabic words.

According to the comfortableness assessment system 100 of the present embodiment, as a user merely hears an audio and thinks of a corresponding hiragana, a determination can be made as to how hard the user has strived (strife) and how annoyed the user was (annoyance) in speech sound listening. As a result, a quantification of comfortableness at speech sound listening is realized, and an acoustic aiding process can be assessed from the perspective of comfortableness, thus permitting a fitting not inducing aural fatigue, through a highly comfortable acoustic aiding process.

In the description of the present embodiment, the biological signal measurement section 50 is illustrated as cutting out an event-related potential in a predetermined range based on a trigger from the presented-speech sound determination section 70 as a starting point, subjecting it to a baseline correction, and sending potential waveform data to the event-related potential processing section 55. However, this process is an example. As another process, for example, the biological signal measurement section 50 may constantly measure an electroencephalogram, cut out an event-related potential as needed by the event-related potential processing section 55, and subject it to a baseline correction. With such a construction, the presented-speech sound determination section 70 does not need to send a trigger to the biological signal measurement section 50, and may only send a trigger to the event-related potential processing section 55.

Although the present embodiment illustrates that the comfortableness assessment results are accumulated in the result accumulating DB 80, accumulation is not necessary. For example, in the case where the result accumulating DB 80 is provided external to the comfortableness assessment apparatus 1, the positive component determination section 60 and the negative component determination section 65 may simply output their respective results of determination. Each result of determination can be utilized as information concerning comfortableness of speech sound listening.

It is illustrated above that the positive component determination section 60 and the negative component determination section 65 determine the presence or absence of the positive component and the negative component, respectively, and output their respective determination results. However, this construction is exemplary. For example, the positive component determination section 60 may determine that there is a high index of strife when the positive component is present, and the negative component determination section 65 may determine that there is a high index of annoyance when the negative component is present. Alternatively, in accordance with the results of determination, an assessment result as to whether speech sound listening required strife or not and an assessment result as to whether acoustic annoyance was felt or not may be output, and accumulated in the result accumulating DB 80. The choice as to which one of a determination result or an assessment result is to be output can be independently set for each of the positive component determination section 60 and the negative component determination section 65.

Note that a determination result may be output in terms of two numerical values representing whether the positive/negative component is present or not, or output in any non-numerical form representing the presence or absence of the positive/negative component (e.g., text information). An assessment result as to whether speech sound listening required strife or not and an assessment result as to whether acoustic annoyance was felt or not may each be output in terms of two numerical values, or degrees of strife and/or annoyance felt may be output in terms of (three or more) numerical values. Alternatively, they may be output in any non-numerical form representing such degrees (e.g., text information).

5. Embodiment 2

In the comfortableness assessment system 100 of Embodiment 1, according to one type of acoustic aiding process stored in the speech sound DB 71, strife and annoyance in speech sound listening are determined for predetermined audios that have been previously adjusted, based on the presence or absence of a positive component at a latency of about 750 ms and a negative component at a latency of about 200 ms.

However, due to increasing precision in the signal processing of the recent years, acoustic aiding processing methods for realizing functions such as consonant emphasis, directivity, and noise reduction, are under development, which make it difficult to search for and identify an optimum acoustic aiding process based on the comfortableness assessment results for a single acoustic aiding process alone.

Therefore, the present embodiment will illustrate a comfortableness assessment system including an acoustic aiding processing section which modifies presented speech sounds into sounds to be output through a hearing aid, and assesses comfortableness for each one of different acoustic aiding processes.

Figure 18:
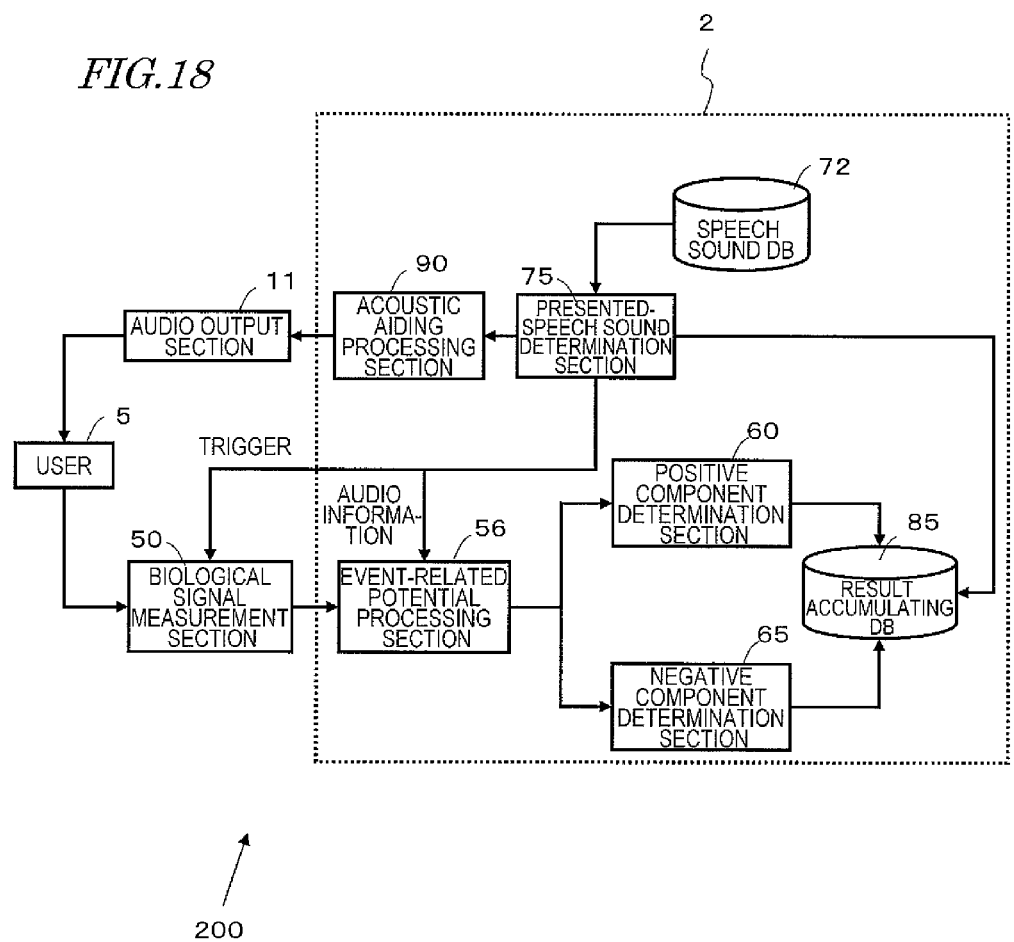
FIG. 18 is a diagram showing the functional block construction of a comfortableness assessment system 200 according to Embodiment 2.

FIG. 18 shows a functional block construction of a comfortableness assessment system 200 of the present embodiment. The comfortableness assessment system 200 includes an audio output section 11, a biological signal measurement section 50, and a speech sound listening comfortableness assessment apparatus 2. Any block which has an identical counterpart in FIG. 12 is denoted by a like reference numeral, and the description thereof is omitted. The hardware construction of the speech sound listening comfortableness assessment apparatus 2 is as shown in FIG. 11.

The speech sound listening comfortableness assessment apparatus 2 of the present embodiment shown in FIG. 18 is realized as a program which defines a different process from that of the program 35 described in Embodiment 1 (FIG. 11) is executed.

One large difference of the speech sound listening comfortableness assessment apparatus 2 of the present embodiment from the speech sound listening comfortableness assessment apparatus 1 of Embodiment 1 is that an acoustic aiding processing section 90 is additionally introduced. Although each component element of the comfortableness assessment apparatus 2 is basically given the same name as that used in Embodiment 1, they may be denoted by different reference numerals when having different operations and/or functions. For example, the present embodiment performs a comfortableness assessment for each of a plurality of acoustic aiding processes, which is not performed in Embodiment 1; therefore, in the place of the event-related potential processing section 55, the presented-speech sound determination section 70, the speech sound DE 71, and the result accumulating DB 80 of Embodiment 1, the present embodiment employs an event-related potential processing section 56, a presented-speech sound determination section 75, a speech sound DB 72, and a result accumulating DB 85.

Hereinafter, the speech sound DB 72, the presented-speech sound determination section 75, the acoustic aiding processing section 90, the event-related potential processing section 56, the result accumulating DB 85, and the acoustic aiding processing section 90 will be described.

Similarly to the speech sound DB 71 of Embodiment 1, the speech sound DB 72 is a speech sound database with which to conduct a comfortableness assessment of speech sound listening, as in the 20 speech sounds of the 67S list shown in FIG. 13, for example. The speech sound DB 72 differs from the speech sound DB 71 in that it contains speech sound data before being subjected to an acoustic aiding process.

Similarly to the presented-speech sound determination section 70 of Embodiment 1, the presented-speech sound determination section 75 determines a speech sound type and a sound pressure level by referring to the speech sound DB. The presented-speech sound determination section 75 differs from the presented-speech sound determination section 70 in that it allows a selection as to which acoustic aiding process an audio is to be modified through, and it sends also the audio data of the speech sound for presentation to the acoustic aiding processing section 90.

Based on the instruction concerning the acoustic aiding process to be selected and the audio data received from the presented-speech sound determination section 75, the acoustic aiding processing section 90 modifies the audio data with the designated acoustic aiding processing method. The acoustic aiding process may involve consonant emphasis, directivity, noise reduction, etc., for example. In the case where an acoustic aiding process involving consonant emphasis is selected, for example, a process of increasing the amount of gain amplification for consonant frequencies than usual is performed, thus modifying the audio data.

Similarly to the event-related potential processing section 55 of Embodiment 1, in accordance with the actual audio to be presented which is received from the presented-speech sound determination section 75, the event-related potential processing section 56 performs an arithmetic mean calculation for the event-related potentials received from the biological signal measurement section 50. A difference from the event-related potential processing section 55 is that, upon receiving the information of an acoustic aiding process from the presented-speech sound determination section 75, the event-related potential processing section 56 performs an arithmetic mean calculation with respect to each speech sound, each sound pressure level, and each acoustic aiding process.

Similarly to the result accumulating DB 80 of Embodiment 1, the result accumulating DB 85 accumulates information received from the positive component determination section 60 concerning the presence or absence of a positive component at a latency of about 750 ms and information received from the negative component determination section 65 concerning the presence or absence of a negative component at a latency of about 200 ms, e.g., with respect to each speech sound and each sound pressure level. A difference from the result accumulating DB 80 is that, from the presented-speech sound determination section 75, the result accumulating DB 85 receives not only information of the speech sound and sound pressure level of the presented stimulation, but also information of an acoustic aiding process type, and accumulates the data with respect to each acoustic aiding process type.

FIGS. 19A and 19B show examples of data accumulation in the result accumulating DB 85. FIGS. 19A and 19B illustrate examples where results of strife and annoyance determinations are accumulated with respect to each speech sound, each sound pressure level, and each acoustic aiding process. For example, FIG. 19A shows results of strife and annoyance determinations accumulated in the result accumulating DB 85 with respect to each speech sound and each sound pressure level, under a certain acoustic aiding process A. FIG. 19B shows results of strife and annoyance determinations accumulated in the result accumulating DB 85 with respect to each speech sound and each sound pressure level, under a certain acoustic aiding process B. In FIGS. 19A and 19B, "1" indicates the case where the positive component determination section 60 or the negative component determination section 65 determines that the positive component or the negative component is present, and "0" indicates the case where the positive component or the negative component is determined to be absent.

Next, with reference to FIG. 20, an overall procedure of processing that is performed in the comfortableness assessment system 200 will be described.

Figure 20:
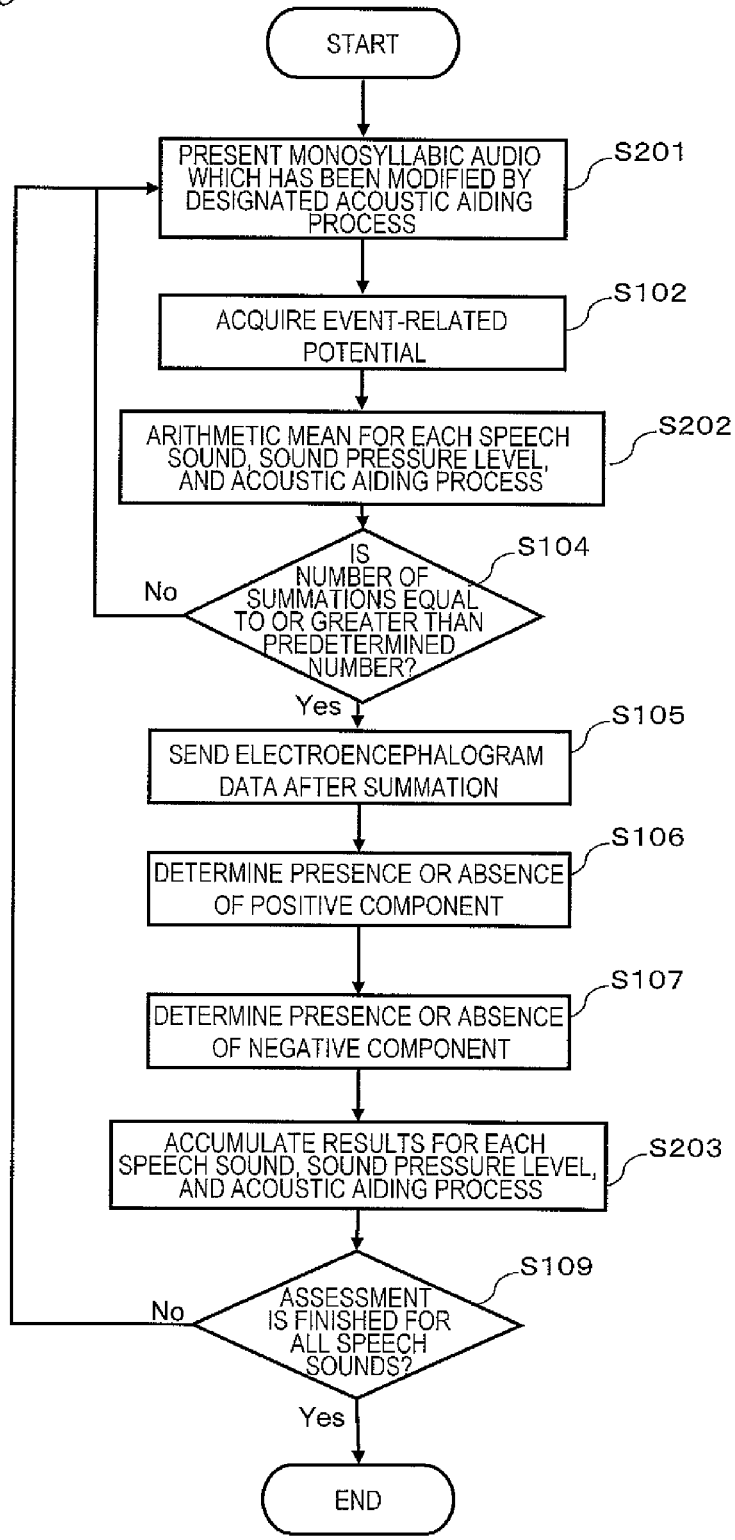
FIG. 20 is a flowchart showing a processing procedure by the speech sound intelligibility system 200 of Embodiment 2.

FIG. 20 is a flowchart showing the processing procedure by the speech sound intelligibility system 200 of the present embodiment. In FIG. 20, any step where a process identical to a process by the comfortableness assessment system 100 (FIG. 16) will be denoted by a like reference numeral, and the description thereof will be omitted.

The processes by the comfortableness assessment system 200 of the present embodiment differ from the processes by the comfortableness assessment system 100 of Embodiment 1 in steps S201, S202, and S203. At step S201, a monosyllabic audio which is modified through the designated acoustic aiding process is presented. At step S202, an arithmetic mean calculation is performed with respect to each speech sound, each sound pressure level, and each acoustic aiding process. At step S203, results are accumulated with respect to each speech sound, each audio, and each acoustic aiding process. Any other steps have already been described in connection with FIG. 16, and the descriptions thereof are omitted.

Hereinafter, steps S201 to S203 will be described in detail.

At step S201, the presented-speech sound determination section 75 determines the type and sound pressure level of the audio to be presented by referring to the speech sound DB 72, and acquires the data thereof. Furthermore, the presented-speech sound determination section determines an acoustic aiding process, and sends the information concerning the acoustic aiding process type and the audio data to the acoustic aiding processing section 90. The acoustic aiding processing section 90 determines the information concerning the acoustic aiding process type as determined by the presented-speech sound determination section 75 and the audio data, and modifies the audio data based on the designated acoustic aiding processing method. The audio output section 11 presents the modified audio data to the user 5.

At step S202, information of the type of speech sound for presentation, sound pressure level, and acoustic aiding process received from the presented-speech sound determination section 75, the event-related potential processing section 56 takes an arithmetic mean of the event-related potential of the electroencephalogram measured by the biological signal measurement section 50, e.g., with respect to each speech sound, each sound pressure level, and each acoustic aiding process.

At step S203, with respect to each of the pieces of information concerning the speech sound for presentation (speech sound type, sound pressure level, acoustic aiding process) received from the presented-speech sound determination section 75, the result accumulating DB accumulates the presence/absence result of a positive component at a latency of about 750 ms as determined by the positive component determination section 60 and the presence/absence result of a negative component at a latency of about 200 ms as determined by the negative component determination section 65. Examples of accumulated results are shown in FIGS. 19A and 19B.

Figure 21:
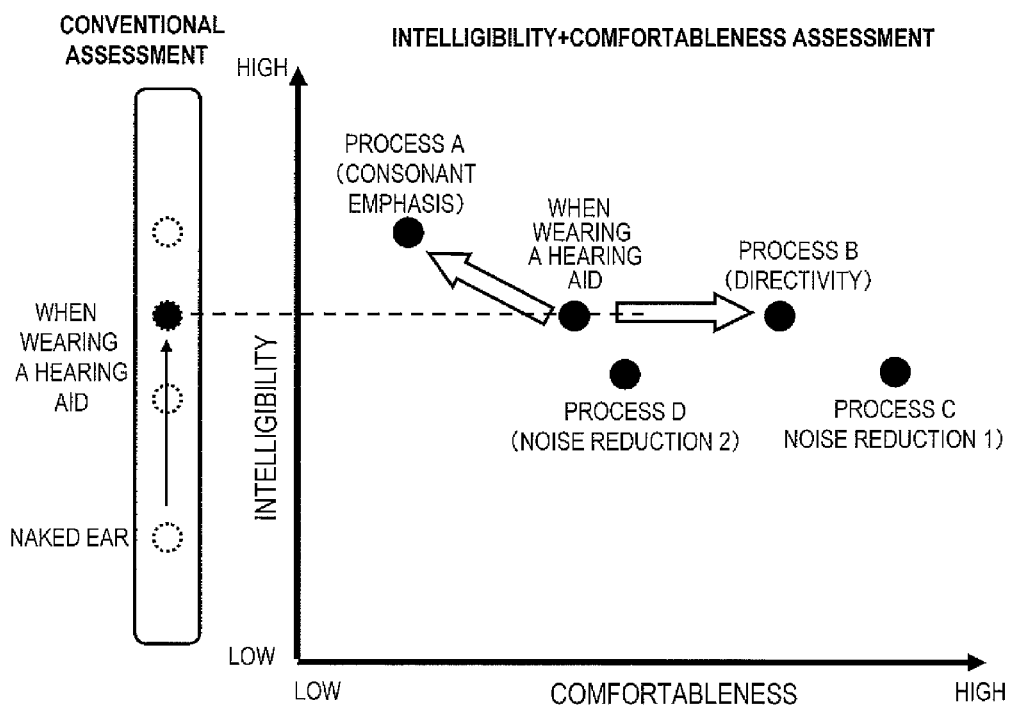
FIG. 21 is a conceptual diagram showing, in the case where speech sounds are presented at a certain sound pressure level, results of a conventional speech sound intelligibility assessment, and results of additionally employing results of a comfortableness assessment according to Embodiment 2.

Through such processes, comfortableness in speech sound listening can be assessed, e.g., with respect to each acoustic aiding process such as consonant emphasis, directivity, or noise reduction. FIG. 21 is a conceptual diagram showing, in the case where speech sounds are presented at a certain sound pressure level, results of a conventional speech sound intelligibility assessment, and results of additionally employing the comfortableness assessment results according to the present embodiment. In FIG. 21, it is contemplated that process A is an acoustic aiding process of consonant emphasis, process B is that of directivity, and process C and process D are those of noise reduction. The respective plotting is based on the following hypotheses.

consonant emphasis (process A): Since the amount of gain adjustment in the consonant frequency band is increased, intelligibility is improved, but comfortableness is deteriorated because the frequency characteristics of the audio itself are affected.

directivity (process B): Although intelligibility does not change in itself, noises ascribable to impertinent sound sources are reduced, so that comfortableness is improved.

noise reduction (processes C and D): Intelligibility is lowered because not only noise but also audio information is subjected to reduction; however, comfortableness is improved due to reduced acoustic annoyance.

Conventionally, based on the results of a speech sound intelligibility assessment alone, only an intelligibility with respect to each given acoustic aiding process is assessed; therefore, process C and process D would be associated with poor suitability, for example. On the other hand, additionally introducing the perspective of comfortableness enables more appropriate assessments of the effects of such acoustic aiding processes.

With the comfortableness assessment system 200 of the present embodiment, comfortableness can be assessed with respect to each acoustic aiding process. This allows an acoustic aiding process to be selected in accordance with the purpose of wearing a hearing aid or the environment of use.

6. Embodiment 3

In the comfortableness assessment system 100 of Embodiment 1, the presence or absence of the positive component and the presence or absence of the negative component are respectively determined at the positive component determination section 60 and the negative component determination section 65, by using a threshold value which is calculated from the positive component/negative component of a generic user, or a template of the positive component/negative component of a generic user.

However, since event-related potential waveforms have large individual differences, accurate determinations of strife and annoyance may be difficult to make through identification on that basis.

Accordingly, in the present embodiment, prior to comfortableness assessment of speech sound listening, a calibration is made for measuring the traits of a positive component at a latency of about 750 ms and a negative component at a latency of about 200 ms of each user, and comfortableness is assessed based on the component traits of each individual person.

Figure 22:
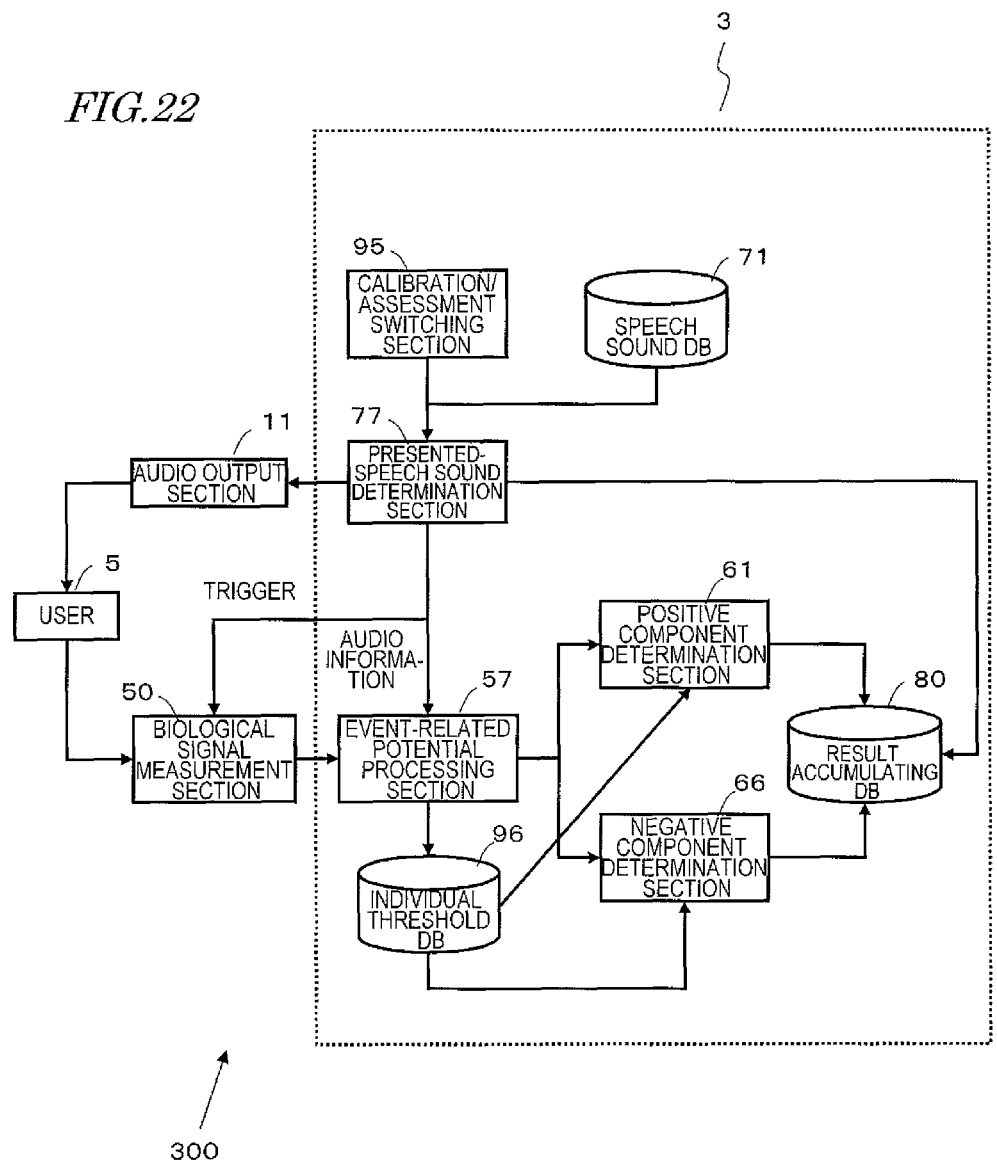
FIG. 22 is a diagram showing the functional block construction of a comfortableness assessment system 300 according to Embodiment 3.

FIG. 22 shows a functional block construction of a comfortableness assessment system 300 of the present embodiment. The comfortableness assessment system 300 includes an audio output section 11, a biological signal measurement section 50, and a speech sound listening comfortableness assessment apparatus 3. Any block which has an identical counterpart in FIG. 12 is denoted by a like reference numeral, and the description thereof is omitted. The hardware construction of the speech sound listening comfortableness assessment apparatus 3 is as shown in FIG. 11. The speech sound listening comfortableness assessment apparatus 3 of the present embodiment shown in FIG. 22 is realized as a program which defines a different process from that of the program 35 described in Embodiment 1 (FIG. 11) is executed.

One large difference of the speech sound listening comfortableness assessment apparatus 3 of the present embodiment from the speech sound listening comfortableness assessment apparatus 1 of Embodiment 1 is that a calibration/assessment switching section 95 and an individual threshold DB 96 are additionally introduced. Moreover, in order to determine the presence or absence of the positive component based on the component trait of each user, the present embodiment employs a positive component determination section 61, a negative component determination section 66, an event-related potential processing section 57, and a presented-speech sound determination section 77, in the place of the event-related potential processing section 55, the positive component determination section 60, the negative component determination section 65, and the presented-speech sound determination section 70 of Embodiment 1.

Hereinafter, the calibration/assessment switching section 95, the individual threshold DB 96, the presented-speech sound determination section 77, the event-related potential processing section 57, the positive component determination section 61, and the negative component determination section 65 will be described.

The calibration/assessment switching section 95 switches between a calibration mode for identifying the traits of event-related potential components of each user and an assessment mode of making a comfortableness assessment. Then, the calibration/assessment switching section 95 sends information representing the current mode to the presented-speech sound determination section 77. Note that the mode switching may be conducted after a predetermined number of times of speech sound presentation that is required for identifying the traits of the user electroencephalogram are finished.

Similarly to the presented-speech sound determination section 70, the presented-speech sound determination section 77 refers to the speech sound DB 71 to determine a speech sound type and a sound pressure level of the presented audio. Moreover, if the information of the calibration mode/assessment mode received from the calibration/assessment switching section 95 indicates the calibration mode, the audio is presented to the user 5 via the audio output section 11 at: (1) a sound pressure level at which the user can hear without strife but which is felt as "annoying", and (2) a sound pressure level at which strife is required but which is felt as "not annoying". The sound pressure level may be determined based on the user's audiogram, for example. Then, the presented-speech sound determination section 77 sends trigger information to the biological signal measurement section 50, and sends the audio information and the calibration/assessment mode information to the event-related potential processing section 57.

Similarly to the event-related potential processing section 55, the event-related potential processing section 57 performs an arithmetic mean calculation for the event-related potentials received from the biological signal measurement section 50, in accordance with the actual audio to be presented which is received from the presented-speech sound determination section 77. The event-related potential processing section 57 receives the mode information from the presented-speech sound determination section 77. If the calibration mode is indicated, an arithmetic mean calculation may be performed with respect to each sound pressure level, irrespective of the speech sound type, for example. Then, trait parameters to be used for identification at the positive component determination section 61 and the negative component determination section 66 are calculated, and sent to the individual threshold DB 96. The trait parameters may each be a zone average potential, maximum amplitude, and the waveform itself. If the assessment mode is indicated, an arithmetic mean calculation is performed by a method similar to that of the event-related potential processing section 55.

The individual threshold DB 96 stores the trait parameters to be used for identification, which have been sent from the event-related potential processing section 57.

Receiving the electroencephalogram data from the event-related potential processing section 57, the positive component determination section 61 and the negative component determination section 66 respectively determine strife and annoyance by referring to the trait parameters with respect to each sound pressure level as stored in the individual threshold DB 96. For example, in the case where the trait parameters are zone average potentials, a positive component/negative component is detected by using an intermediate value of the trait parameter with respect to each sound pressure level as a threshold value, through a method similar to that of the positive component determination section 60/negative component determination section 65.

Next, with reference to FIG. 23, an overall procedure of processing performed by the comfortableness assessment system 300 will be described.

Figure 23:
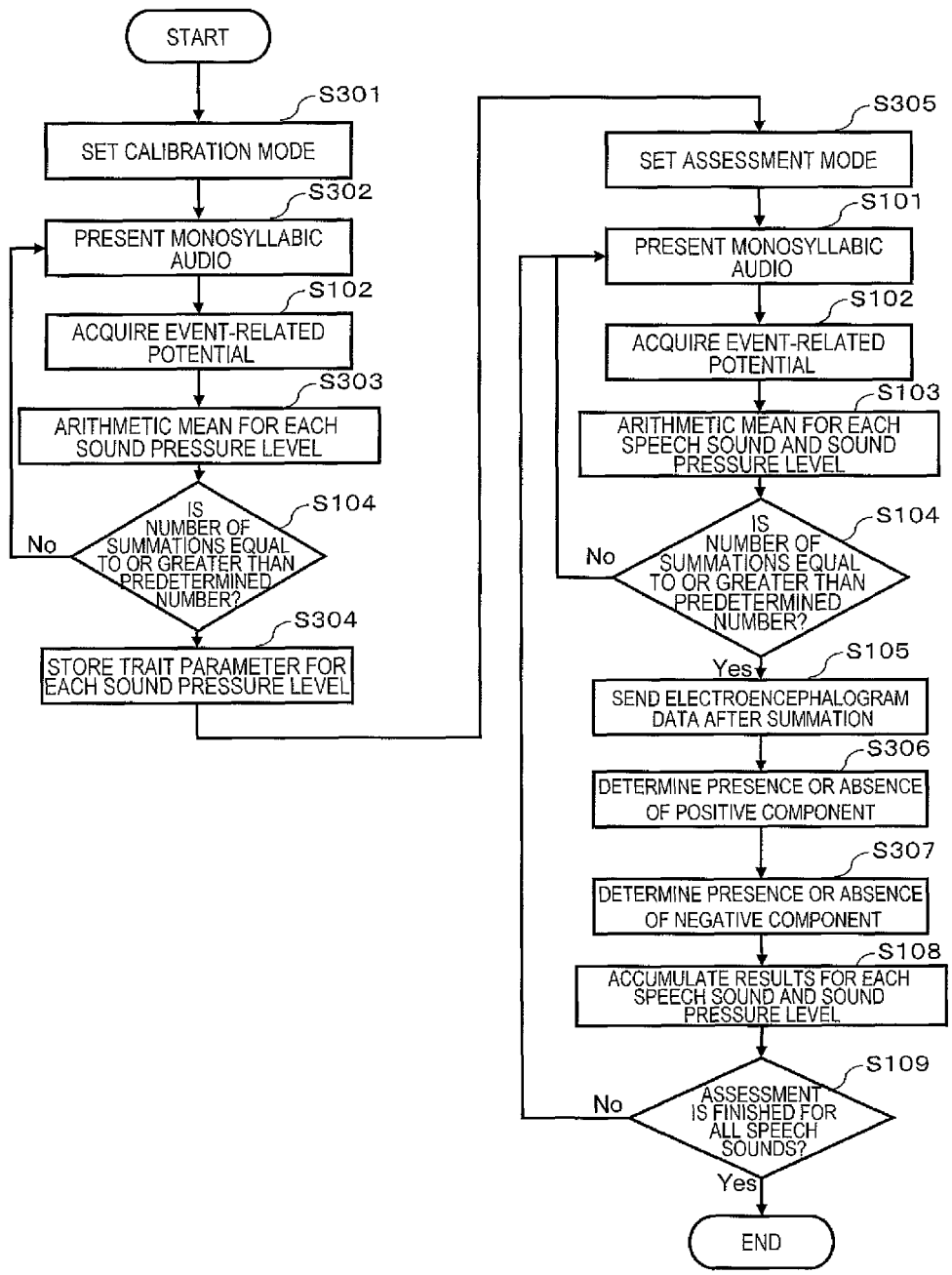
FIG. 23 is a flowchart showing a processing procedure by the speech sound intelligibility system 300 of Embodiment 3.

FIG. 23 is a flowchart showing the processing procedure by the speech sound intelligibility system 300 of the present embodiment. In FIG. 23, any step where a process identical to a process by the comfortableness assessment system 100 (FIG. 16) will be denoted by a like reference numeral, and the description thereof will be omitted.

The processes by the comfortableness assessment system 300 of the present embodiment differ from the processes by the comfortableness assessment system 100 of Embodiment 1 in steps S301 to S308. Any other steps have already been described in connection with FIG. 16, and the descriptions thereof are omitted.

At step S301, based on a selection by the user, the calibration/assessment switching section 95 sets the current mode to the calibration mode, and sends information indicating the calibration mode to the presented-speech sound determination section 77.

At step S302, the presented-speech sound determination section 77 determines a speech sound type by referring to the speech sound DB 71. Then, regarding monosyllabic audio presentation, the presented-speech sound determination section 77 sets either a (1) a sound pressure level at which the user can hear without strife but which is felt as "annoying", or (2) a sound pressure level at which strife is required but which is felt as "not annoying". Then, an audio is presented to the user 5 via the audio output section 11.

At step S303, the event-related potential processing section 57 takes an arithmetic mean of the event-related potential measured by the biological signal measurement section 50 with respect to each sound pressure level.

At step S304, the event-related potential processing section 57 stores trait parameters with respect to each sound pressure level. More specifically, from the arithmetic mean waveform, the event-related potential processing section 57 calculates trait parameters to be used for identification at the positive component determination section 61 and the negative component determination section 66. For example, in the case where each trait parameter is a zone average potential, an average potential in a predetermined zone is calculated. Then, these are stored to the individual threshold DB 96. The average values thus obtained can be considered representative of traits that are unique to that user.

At step S305, after a predetermined number of times of audio presentation are finished, the calibration/assessment switching section 95 switches from the calibration mode to the assessment mode, and sends information indicating the assessment mode to the presented-speech sound determination section 77.

At step S306, presence or absence of the positive component is determined based on the trait parameter concerning the positive component of each user. Specifically, the positive component determination section 61 refers to the individual threshold DB 96 to read a threshold value for determining the presence or absence of a positive component therefrom, and by using this threshold value, determines the presence or absence of a positive component at a latency of about 750 ms in the event-related potential received from the event-related potential processing section 57. For example, in the case of employing a zone average potential as the trait parameter for identification, if the zone average potential at a latency from about 750 ms is greater than the calculated threshold value, it is determined that the positive component is present; if the zone average potential is smaller, it is determined that the positive component is absent.

At step S307, presence or absence of the negative component is determined based on a trait parameter concerning the negative component of each user. Specifically, at step S307, the negative component determination section 61 refers to the individual threshold DB 96 to read a threshold value for determining the presence or absence of a negative component therefrom, and by using this threshold value, determines the presence or absence of a negative component at a latency of about 200 ms in the event-related potential received from the event-related potential processing section 57. For example, in the case of employing latency as the trait parameter for identification, if the latency of the negative component peak is smaller than the calculated threshold value, it is determined that the negative component is present; if the latency is greater, it is determined that the negative component is absent.

Through such processes, it is possible to identify the presence or absence of the positive component and the negative component in accordance with the electroencephalographic traits of each user, thus enabling an accurate assessment of comfortableness of speech sound listening.

With the comfortableness assessment system 300 of the present embodiment, comfortableness can be highly accurately assessed in accordance with the electroencephalographic traits of each user. As a result, an acoustic aiding process which is highly comfortable and not inducing aural fatigue can be realized.

Although the present embodiment illustrates that a calibration is performed for both trait parameters of the positive component and negative component of each user, such processes are exemplary. Alternatively, only one of the positive component and the negative component may be subjected to calibration as a trait parameter of each user.

With a speech sound listening comfortableness assessment apparatus according to the present disclosure and a speech sound listening intelligibility assessment system in which the speech sound listening comfortableness assessment apparatus is incorporated, in addition to assessing an intelligibility as to whether a speech sound has been aurally distinguished or not, a quantitative assessment of comfortableness in speech sound listening can be made based on an electroencephalogram during speech sound listening. Since this permits selection of an acoustic aiding process which is highly comfortable and not inducing aural fatigue, the present disclosure is available to the fitting of any and all hearing aid users.

While the present invention has been described with respect to exemplary embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An assessment system of speech sound listening, comprising:
    a biological signal measurement unit configured to measure an electroencephalogram signal of a user;
    a presented-speech sound determination unit configured to determine a monosyllabic speech sound to be presented, by referring to a speech sound database retaining a plurality of monosyllabic speech sounds;
    an output unit configured to present a speech sound determined by the presented-speech sound determination unit to the user as an auditory stimulation;
    a positive component determination unit configured to determine a strife parameter concerning how much effort has been made to aurally distinguish the speech sound based on whether a positive component appears in an event-related potential of the electroencephalogram signal in a range from 600 ms to 900 ms from a starting point, the starting point being a point in time at which the speech sound is presented, and configured to output an assessment result as to whether the user is listening to the speech sound with strife or not in accordance with a result of determination; and
    a negative component determination unit configured to determine an annoyance parameter indicating how annoying by loudness the speech sound has been felt based on whether a negative component appears in an event-related potential of the electroencephalogram signal in a range from 100 ms to 300 ms from a starting point, the starting point being the point in time at which the speech sound is presented, and configured to output an assessment result as to whether the user is annoyed by loudness of the speech sound or not in accordance with a result of determination.

2. The assessment system of speech sound listening of claim 1, further comprising an event-related potential processing unit configured to take an arithmetic mean of event-related potentials of the electroencephalogram signal, wherein the speech sound is classified based on at least one of a speech sound type and a sound pressure level of presentation, and the event-related potential processing unit takes an arithmetic mean of event-related potentials of the electroencephalogram signals obtained when speech sounds belonging to a same classification are presented.

3. The assessment system of speech sound listening of claim 1, wherein the positive component determination unit determines that the positive component is present when a zone average potential of an event-related potentials of the electroencephalogram signals in a range from 600 ms to 900 ms from a starting point, the starting point being a point in time at which the speech sound is presented, is equal to or greater than a predetermined first threshold value, and determines that the positive component is absent when the zone average potential is smaller than the first threshold value.

4. The assessment system of speech sound listening of claim 3, wherein the positive component determination unit outputs an assessment result that the user is listening to the speech sound with strife when determining that the positive component is present, and outputs an assessment result that the user is hearing the speech sound without strife when determining that the positive component is absent.

5. The assessment system of speech sound listening of claim 1, wherein the negative component determination unit determines that the negative component is present when a peak latency of a negative component in a range from 100 ms to 300 ms from a starting point, the starting point being a point in time at which the speech sound is presented, is shorter than a predetermined second threshold value, and determines that the negative component is absent when the peak latency of the negative component is equal to or greater than the second threshold value.

6. The assessment system of speech sound listening of claim 5, wherein the negative component determination unit outputs an assessment result that the user is annoyed by the speech sound when determining that the negative component is present, and outputs an assessment result that the user is not annoyed by the speech sound when determining that the negative component is absent.

7. The assessment system of speech sound listening of claim 5, wherein, in the speech sound database, an audio, consonant information, and a group concerning probability of confusion are associated with each of the plurality of speech sounds.

8. The assessment system of speech sound listening of claim 7, further comprising a result accumulating database configured to accumulate results of determination by the positive component determination unit and the negative component determination unit, wherein
with respect to at least one sound pressure level, the result accumulating database calculates a proportion of speech sounds, consonants, or groups concerning probability of confusion for which the positive component determination unit has determined that the positive component is absent, and a proportion of speech sounds, consonants, or groups concerning probability of confusion for which the negative component determination unit has determined that the negative component is absent, and generates assessment results by using results of the calculation.

9. The assessment system of speech sound listening of claim 7, wherein, in a result accumulating database, information for assessing whether the user is listening to the speech sound with strife and whether the user is annoyed by the speech sound is accumulated with respect to each speech sound, each consonant, or each group concerning probability of confusion.

10. The assessment system of speech sound listening of claim 9, wherein, in the result accumulating database, information for assessing whether the user is listening to the speech sound with strife and whether the user is annoyed by the speech sound is accumulated with respect to each speech sound and each sound pressure level.

11. The assessment system of speech sound listening of claim 5, wherein the presented-speech sound determination unit determines a sound pressure level of the presented audio.

12. The assessment system of speech sound listening of claim 5, further comprising an acoustic aiding processing unit configured to select an acoustic aiding process type for the speech sound determined by the presented-speech sound determination unit for presentation, and configured to modify speech sound data retained in the speech sound database based on the selected acoustic aiding process.

13. The assessment system of speech sound listening of claim 12, further comprising a result accumulating database configured to accumulate results of determination by the positive component determination unit and the negative component determination unit, wherein
in the result accumulating database, information for assessing whether the user is listening to the speech sound with strife and whether the user is annoyed by the speech sound is accumulated with respect to each speech sound and each acoustic aiding process.

14. An assessment apparatus of speech sound listening, comprising:
a presented-speech sound determination unit configured to, by referring to a speech sound database retaining a plurality of monosyllabic speech sounds, determine one of the monosyllabic speech sounds to be presented via an output unit to a user as an auditory stimulation;
a positive component determination unit configured to, with respect to an electroencephalogram signal measured by a biological signal measurement unit for measuring an electroencephalogram signal of the user, determine a strife parameter concerning how much effort has been made to aurally distinguish the speech sound based on whether a positive component appears in an event-related potential of the electroencephalogram signal in a range from 600 ms to 900 ms from a starting point, the starting point being a point in time at which the speech sound is presented; and
a negative component determination unit configured to determine an annoyance parameter indicating how annoying by loudness the speech sound has been felt based on whether a negative component appears in an event-related potential of the electroencephalogram signal in a range from 100 ms to 300 ms from a starting point, the starting point being the point in time at which the speech sound is presented.

15. A assessment method of speech sound listening, comprising the steps of:
measuring an electroencephalogram signal of a user;
determining a monosyllabic speech sound to be presented, by referring to a speech sound database retaining a plurality of monosyllabic speech sounds;
presenting a speech sound determined by the step of determining to the user as an auditory stimulation;
determining a strife parameter concerning how much effort has been made to aurally distinguish the speech sound based on whether a positive component appears in an event-related potential of the electroencephalogram signal in a range from 600 ms to 900 ms from a starting point, the starting point being a point in time at which the speech sound is presented;
outputting an assessment result as to whether the user is listening to the speech sound with strife or not in accordance with a result of determination;
determining an annoyance parameter indicating how annoying by loudness the speech sound has been felt based on whether a negative component appears in an event-related potential of the electroencephalogram signal in a range from 100 ms to 300 ms from a starting point, the starting point being the point in time at which the speech sound is presented; and
outputting an assessment result as to whether the user is annoyed by loudness of the speech sound or not in accordance with a result of determination.

16. A non-transitory computer readable medium storing a computer program to be executed by a computer mounted in a speech sound intelligibility assessment system, wherein the computer program causes the computer in the speech sound intelligibility assessment system to execute the steps of:

receiving a measured electroencephalogram signal of a user;

determining a monosyllabic speech sound to be presented, by referring to a speech sound database retaining a plurality of monosyllabic speech sounds;

presenting a speech sound determined by the step of determining to the user as an auditory stimulation;

determining a strife parameter concerning how much effort has been made to aurally distinguish the speech sound based on whether a positive component appears in an event-related potential of the electroencephalogram signal in a range from 600 ms to 900 ms from a starting point, the starting point being a point in time at which the speech sound is presented;

outputting an assessment result as to whether the user is listening to the speech sound with strife or not in accordance with a result of determination;

determining an annoyance parameter indicating how annoying by loudness the speech sound has been felt based on whether a negative component appears in an event-related potential of the electroencephalogram signal in a range from 100 ms to 300 ms from a starting point, the starting point being the point in time at which the speech sound is presented, and outputting an assessment result as to whether the user is annoyed by loudness of the speech sound or not in accordance with a result of determination.

* * * * *